United States Patent
Daniely et al.

(10) Patent No.: US 9,851,354 B2
(45) Date of Patent: Dec. 26, 2017

(54) METHODS OF TREATING FRAGILE X SYNDROME AND RELATED DISORDERS

(71) Applicant: Alcobra Ltd., Tel Aviv (IL)

(72) Inventors: Yaron Daniely, Tel Aviv (IL); Dalia Megiddo, Nataf (IL)

(73) Assignee: Alcobra Ltd., Tel Aviv (IL)

( * ) Notice: Subject to any disclaimer, the term of this patent is extended or adjusted under 35 U.S.C. 154(b) by 0 days.

(21) Appl. No.: 14/917,169

(22) PCT Filed: Sep. 9, 2014

(86) PCT No.: PCT/IB2014/002398
§ 371 (c)(1),
(2) Date: Mar. 7, 2016

(87) PCT Pub. No.: WO2015/033224
PCT Pub. Date: Mar. 12, 2015

(65) Prior Publication Data
US 2016/0193199 A1    Jul. 7, 2016

Related U.S. Application Data

(63) Continuation of application No. 14/038,258, filed on Sep. 26, 2013, now abandoned.
(Continued)

(51) Int. Cl.
*A61K 31/4439* (2006.01)
*G01N 33/573* (2006.01)
(Continued)

(52) U.S. Cl.
CPC ......... *G01N 33/573* (2013.01); *A61K 9/0053* (2013.01); *A61K 31/4015* (2013.01);
(Continued)

(58) Field of Classification Search
CPC .......... A61K 8/97; A61K 8/368; A61K 8/365; A61Q 19/08
See application file for complete search history.

(56) References Cited

U.S. PATENT DOCUMENTS

| | | | |
|---|---|---|---|
| 4,313,952 A | 2/1982 | Baldacci | |
| 8,476,304 B2 | 7/2013 | Megiddo et al. | |

(Continued)

FOREIGN PATENT DOCUMENTS

| | | | |
|---|---|---|---|
| WO | WO 2002/043507 A2 | 6/2002 | |
| WO | WO 2009/004629 A2 | 1/2009 | |

(Continued)

OTHER PUBLICATIONS

Holzman et al (Drugs.com, http://www.drugs.com/clinical_trials/teva-alcobra-announce-phase-ii-trial-novel-non-stimulant-mg01ci-adhd-meets-primary-endpoint-12311.html, published Sep. 2011).*

(Continued)

*Primary Examiner* — Savitha Rao
*Assistant Examiner* — Angela Brown-Pettigrew
(74) *Attorney, Agent, or Firm* — Cooley LLP; Ivor Elrifi; Cynthia Kozakiewicz

(57) ABSTRACT

The present invention provides methods of alleviating a sign or a symptom of Fragile X Syndrome and relates disorders such as autism spectrum disorders.

8 Claims, 16 Drawing Sheets

Related U.S. Application Data

(60) Provisional application No. 61/991,351, filed on May 9, 2014, provisional application No. 61/875,384, filed on Sep. 9, 2013.

(51) Int. Cl.
    A61K 31/4425    (2006.01)
    A61K 31/4015    (2006.01)
    A61K 9/00       (2006.01)

(52) U.S. Cl.
    CPC ...... A61K 31/4425 (2013.01); A61K 31/4439 (2013.01); G01N 2333/91205 (2013.01); G01N 2440/14 (2013.01); G01N 2800/30 (2013.01); G01N 2800/52 (2013.01)

(56) References Cited

U.S. PATENT DOCUMENTS

| | | |
|---|---|---|
| 8,710,067 B2 | 4/2014 | Yamin et al. |
| 2010/0256198 A1 | 10/2010 | Megiddo et al. |
| 2012/0264781 A1 | 10/2012 | Yamin et al. |
| 2015/0073023 A1 | 3/2015 | Daniely et al. |
| 2015/0335629 A1 | 11/2015 | Daniely et al. |
| 2016/0216265 A1 | 7/2016 | Daniely et al. |

FOREIGN PATENT DOCUMENTS

| | | |
|---|---|---|
| WO | WO 2010/150261 A1 | 12/2010 |
| WO | WO 2015/033224 A2 | 3/2015 |
| WO | WO 2015/035402 A1 | 3/2015 |

OTHER PUBLICATIONS

Torrioli et al (2010. Treatment with valproic acid ameliorates ADHD symptoms in fragile X syndrome boys. Am J Med Genet Part A 152A:1420-1427).*

Manor et al. (J Clin Psychiatry 73:12, Dec. 2012).*

Reiersen et al (Expert Rev. Neurotherapeutics 8(4), 657-669 (2008)).*

"Attention Deficit Hyperactivity Disorder (ADHD)" California State University, Accessibility Resource Center, printed Apr. 30, 2014 (2 pages).

"FDA Grants Orphan Status to Metadoxine in Fragile X Syndrome" Globenewswire.com News Release, Dec. 18, 2013 (4 pages).

Addolorato, G., et al., "Metadoxine in the treatment of acute and chronic alcoholism: a review." Int. J. Immunopathol. Pharmacol. (2003); 16:207-214.

Cook, N.R., "Use and misuse of the receiver operating characteristic curve in risk prediction." Circulation (2007); 115.7: 928-935.

D'Agostino Sr., et al., "Validation of the Framingham coronary heart disease prediction scores: results of a multiple ethnic groups investigation." JAMA (2001); 286.2: 180-187.

Ethell and Yamaguchi, "Cell surface heparan sulfate proteoglycan syndecan-2 induces the maturation of dendritic spines in rat hippocampal neurons." The Journal of Cell Biology (1999); 144.3: 575-586.

Ethell et al., "EphB/syndecan-2 signaling in dendritic spine morphogenesis." Neuron (2001); 31.6: 1001-1013.

Fraxa Research Foundation, http://www.fraxa.org/neuren-pharmaceuticals-trial-new-drug-autismfragilex/, accessed Jun. 30, 2014.

Henkemeyer et al., "Multiple EphB receptor tyrosine kinases shape dendritic spines in the hippocampus." The Journal of Cell Biology (2003); 163.6: 1313-1326.

Hoeffer et al., "Inhibition of the interactions between eukaryotic initiation factors 4E and 4G impairs long-term associative memory consolidation but not reconsolidation." PNAS (2011); 108(8): 3383-3388.

Klann and Dever, "Biochemical mechanisms for translational regulation in synaptic plasticity." Nature Reviews Neuroscience (2004); 5.12: 931-942.

Langer, "New Methods of Drug Delivery," Science (1990); 249:(4976): 1527-1533.

Lopez Verrilli et al., "Angiotensin-(1-7) through AT2 receptors mediates tyrosine hydroxylase degradation via the ubiquitin-proteasome pathway." Journal of Neurochemistry (2009); 109.2: 326-335.

Lü, Yuan, et al., "Pharmacokinetics of Metadoxine for Injection After Repeated Doses in Healthy Volunteers," Chin. Med. J. (2007); 120(2):160-168.

McCracken et al., "Risperidone in children with autism and serious behavioral problems." N Engl J Med. (2002); 347(5): 314-321.

O'Marcaigh et al., "Estimating the predictive value of a diagnostic test how to prevent misleading or confusing results." Clinical Pediatrics (1993); 32.8: 485-491.

PCT Application No. PCT/IB2014/002398, International Preliminary Report on Patentability dated Mar. 15, 2016, 5 pages.

PCT Application No. PCT/IB2014/002398, International Search Report and Written Opinion dated Nov. 12, 2014, 8 pages.

PCT Application No. PCT/US2014/054816, International Preliminary Report on Patentability dated Mar. 15, 2016, 6 pages.

PCT Application No. PCT/US2014/054816, International Search Report and Written Opinion dated Nov. 12, 2014, 9 pages.

Pepe et al., "Limitations of the odds ratio in gauging the performance of a diagnostic, prognostic, or screening marker." American Journal of Epidemiology (2004); 159.9: 882-890.

Sharma, A., et al. "Dysregulation of mTOR signaling in fragile X syndrome." The Journal of Neuroscience (2010); 30(2): 694-702.

Shultz, "Clinical Interpretation of Laboratory Procedures." Chapter 14 in Teitz, Fundamentals of Clinical Chemistry, Burtis and Ashwood (eds.), 4th Edition (1996), W.B. Saunders Company, pp. 192-199.

Wang et al., "Activation of the extracellular signal-regulated kinase pathway contributes to the behavioral deficit of fragile x-syndrome." Journal of Neurochemistry (2012); 121(4): 672-679.

Wang, Hoau-Yan, et al. "BDNF-trkB signaling in late life cognitive decline and Alzheimer's disease." Translational Neuroscience (2011); 2(2): 91-100.

Weng, N., et al. "Early-phase ERK activation as a biomarker for metabolic status in fragile X syndrome." American Journal of Medical Genetics Part B: Neuropsychiatric Genetics (2008); 147(B): 1253-1257.

Zweig et al., "ROC curve analysis: an example showing the relationships among serum lipid and apolipoprotein concentrations in identifying patients with coronary artery disease." Clinical Chemistry (1992); 38.8: 1425-1428.

Liu, Zhong-Hua, et al. "Lithium reverses increased rates of cerebral protein synthesis in a mouse model of fragile X syndrome." Neurobiology of Disease (2012); 45.3: 1145-1152.

Paul, L., et al., "Dampened dopamine-mediated neuromodulation in prefrontal cortex of fragile X mice." J Physiol (2013); 591.4: 1133-1143.

* cited by examiner

METHODS OF TREATING FRAGILE X SYNDROME AND RELATED DISORDERS

RELATED APPLICATIONS

This application is the National Stage of International Application No. PCT/IB2014/002398, filed Sep. 9, 2014, which claims priority to and benefit of provisional application U.S. Ser. No. 61/875,384 filed on Sep. 9, 2013, U.S. Ser. No. 14/038,258 filed Sep. 26, 2013 and provisional application U.S. Ser. No. 61/991,351 filed May 9, 2014. The contents of each above-listed application are herein incorporated by reference in their entireties.

FIELD OF THE INVENTION

The present invention relates generally to methods of treating or alleviating a symptom of Fragile X syndrome and related disorders.

BACKGROUND OF THE INVENTION

Fragile X Syndrome (FXS), as implied by its name, is associated with a fragile site expressed as an isochromatid gap in the metaphase chromosome at map position Xq 27.3. Fragile X syndrome is a genetic disorder caused by a mutation in the 5'-untranslated region of the fragile X mental retardation 1 (FMR1) gene, located on the X chromosome. The mutation that causes FXS is associated with a CGG repeat in the fragile X mental retardation gene FMR1. In most healthy individuals, the total number of CGG repeats ranges from less than 10 to 40, with an average of about 29. In fragile X syndrome, the CGG sequence is repeated from 200 to more than 1,000 times. When a subject has more than about 200 CGG repeats, the fragile X gene becomes hypermethylated, which silences the gene. As a result, fragile X mental retardation protein (FMRP) is not produced, or is produced at reduced level, and the subject displays manifestations of FXS.

Premutation expansions (55-200 CGG repeats) of the FMR1 gene are frequent in the general population, with estimated prevalences of 1 per 259 females and 1 per 812 males. Carriers of the premutation typically have normal IQ, although emotional problems such as anxiety are common. Older male carriers of the premutation (50 years and older) develop progressive intention tremor and ataxia. These movement disorders are frequently accompanied by progressive cognitive and behavioral difficulties, including memory loss, anxiety, and deficits of executive function, reclusive or irritable behavior, and dementia. This disorder has been designated fragile X-associated tremor/ataxia syndrome (FXTAS). Magnetic resonance imaging in subjects with FXTAS reveals increases in T2-weighted signal intensity in the middle cerebellar peduncles and adjacent cerebellar white matter.

FXS segregates as an X-linked dominant disorder with reduced penetrance. Either sex when carrying the fragile X mutation may exhibit intellectual disability, which is variable in severity. Children and adults with FXS have varying degrees of intellectual disability or learning disabilities and behavioral and emotional problems, including autistic-like features and tendencies. Young children with FXS often have delays in developmental milestones, such as learning how to sit, walk and talk. Affected children may have frequent tantrums, difficulties in paying attention, frequent seizures (e.g., temporal lobe seizures), are often highly anxious, easily overwhelmed, can have sensory hyperarousal disorder, gastrointestinal disorders, and may have speech problems and unusual behaviors, such as hand flapping and hand biting.

FXS can be diagnosed by an established genetic test performed on a sample (e.g., blood sample, buccal sample) from the subject. The test determines whether a mutation or premutation is present in the FMR1 gene of the subject based upon the number of CGG repeats.

Subjects with FXS can also have autism. About 5% of all children diagnosed with autism have a mutation in the FMR1 gene and also have fragile X syndrome (FXS). Autism spectrum disorder (ASD) is seen in approximately 30% of males and 20% of females with FXS, and an additional 30% of FXS individuals display autistic symptoms without having the ASD diagnosis. Although intellectual disability is a hallmark feature of FXS, subjects with FXS often display autistic features ranging from shyness, poor eye contact, and social anxiety in mild cases to hand flapping, hand biting and perseverative speech in the severely affected. Subjects with FXS display other symptoms associated with autism such as attention deficit and hyperactivity, seizures, hypersensitivity to sensory stimuli obsessive-compulsive behavior and altered gastrointestinal function. The FMR1 mutation prevents or greatly decreases expression of a single protein (FMRP). Brain development in the absence of FMRP is thought to give rise to the major symptoms of FXS.

In addition to core symptoms, children with FXS frequently have serious behavioral disturbances such as irritability, aggression and self-injurious behaviors. In a recent study of males with FXS (ages 8-24), self-injurious behavior was reported in 79%, and aggressive behavior in 75%, of subjects during a two month observation period.

Currently available treatment regimens for humans with FXS include, for example, behavioral modifications and treatment with a range of medications (not approved by FDA for the treatment of FXS) including antidepressant and antipsychotic drugs. Cognitive behavioral therapy has been used to improve language and socialization in individuals with FXS and autism. In recent years, pharmacological treatment with the atypical antipsychotic risperidone has been commonly employed to augment non-pharmacological approaches in the treatment of individuals with autism. A randomized placebo-controlled trial of risperidone in autistic children demonstrated significant improvement on the irritability subscale of the Aberrant Behavior Checklist and the Clinical Global Impressions-Improvement (McCracken, J. T., et al., N. Engl. J. Med. 347:314-321 (2002)). However, adverse events included weight gain, increased appetite, fatigue, drowsiness, dizziness, and drooling. Social isolation and communication were not improved by administration of risperidone and adverse side effects such as extrapyramidal symptoms and dyskinesias have been associated with risperidone use in autistic children. Since current treatment regimens are frequently not effective or may produce undesirable side-effects with long term use, particularly in the case of antipsychotic drugs, there is a need to develop new treatments.

SUMMARY OF THE INVENTION

In various aspects the invention provides methods of treating or alleviating a symptom of Fragile X Syndrome or a related disorder by administering to a subject in need thereof a composition comprising metadoxine. The symptom is for example, impaired learning or impaired sociability. The subject has Fragile X Syndrome or an Autism Spectrum Disorder. The related disorder is an Autism Spectrum Disorder.

In some aspects a total per day dose of metadoxine of between 100-3000 mg is administered the metadoxine is administered daily, every other day or weekly.

Optionally, the metadoxine is administered in one, two, or three dosage forms per day. In some embodiments the metadoxine is administered in a sustained release oral dosage form, wherein the metadoxine is formulated as a combination of slow release and immediate release forms.

For example, the slow release form provides for sustained release of the metadoxine for at least 8 hours. The relative proportion of the slow release metadoxine to the immediate release metadoxine is between about 60:40 and 80:20. Preferably, the relative proportion of the slow release metadoxine to the immediate release metadoxine is about 65:35.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

Figure 14:
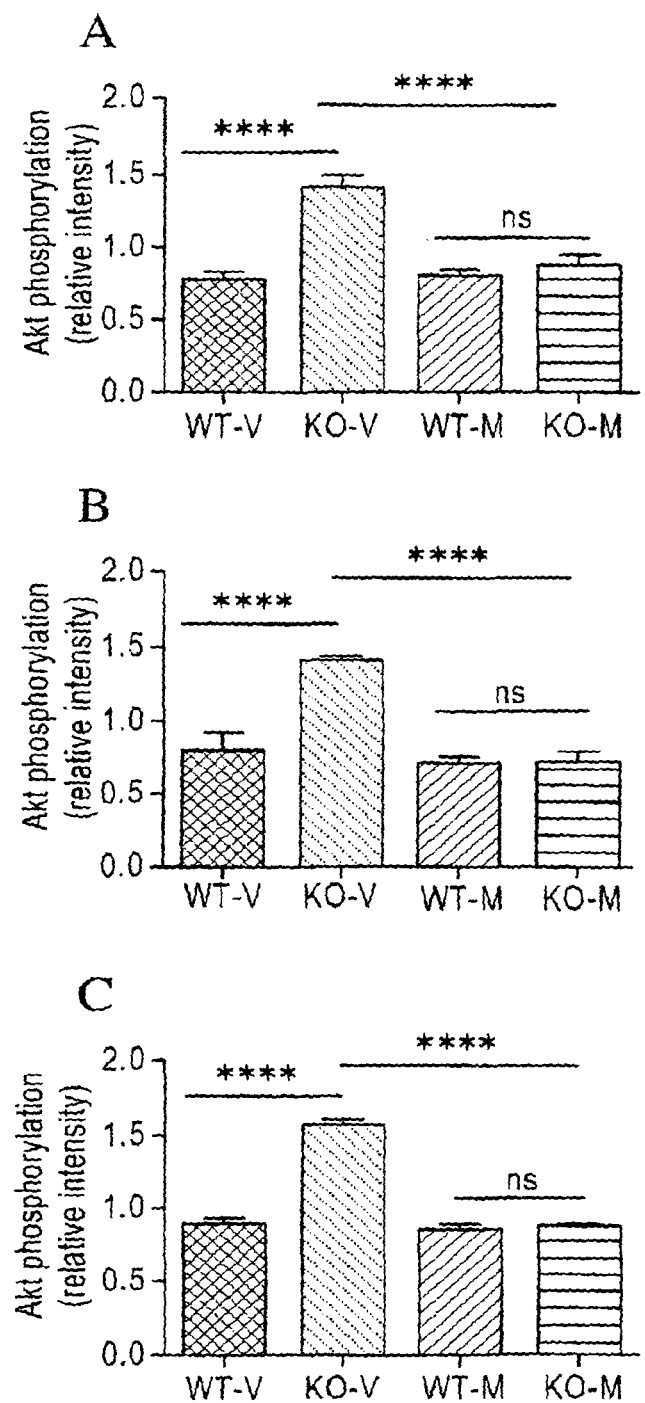

FIG. 14 shows the effect of once daily ip of vehicle (V) or 150 mg/kg metadoxine (M) for 7 days on pAkt levels in brain regions of two month old Wild Type (WT) and Fmr1 knockout (KO) mice. The regions analyzed were the hippocampus (Panel A), pre-frontal cortex (Panel B), and striatum (Panel C) in Fmr1 knockout or Wild Type mice. Data shown are mean±sem, N=10 mice per group. ****p<0.0001 and ns=Not Significant.

Figure 15:
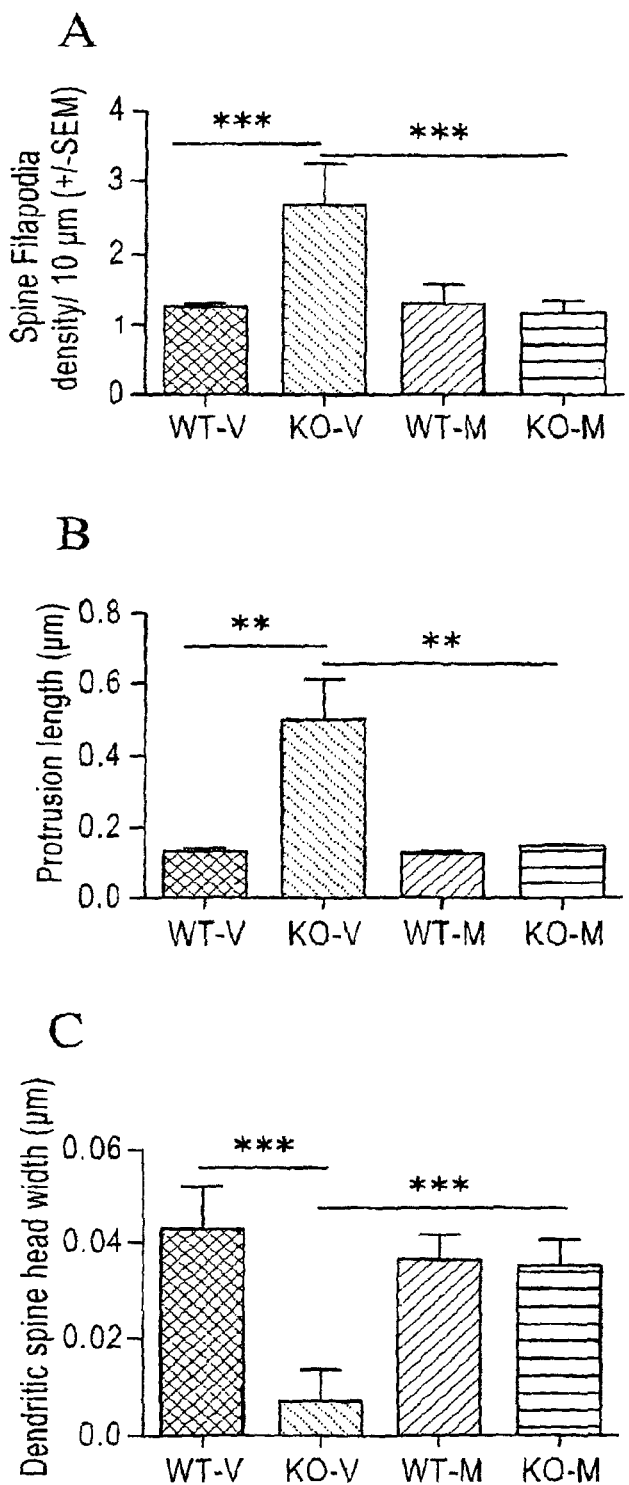

FIG. 15 shows the effect of 5 hour treatment with vehicle (V) or 300 µM metadoxine (M) in vitro on filopodia density (Panel A), length (Panel B), and width (Panel C) in neuronal hippocampal cultures from Fmr1 knockout (KO) or Wild Type (WT) mice. Data shown are mean±sem, (Wild Type, N=20 neurons and Fmr1 knockout mice, N=20 neurons). p<0.01, *p<0.001, and ns=Not Significant.

Figure 16:
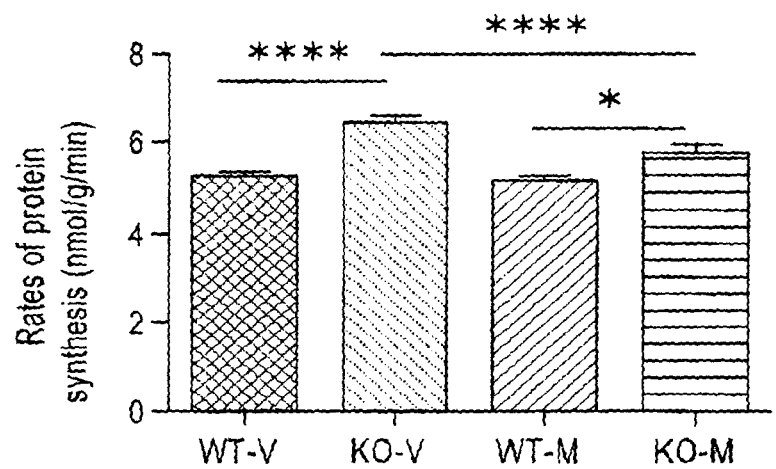

FIG. 16 shows the effect of treatment in vitro with vehicle (V) or 300 µM metadoxine (M) on basal de novo protein synthesis in 400 µM hippocampal slices from Fmr1 knockout (KO) or Wild Type (WT) mice. Data shown are mean±sem, N=6 slices per group. *p<0.001 and ****p<0.0001.

DETAILED DESCRIPTION OF THE INVENTION

The present invention relates to the discovery that metadoxine significantly improves cognitive and social functioning in a valid animal model for the Fragile-X Syndrome.

Specifically, metadoxine significantly improved memory and learning during the contextual fear paradigm in a dose-dependent manner, and the two highest dose levels (150 and 200 mg/kg) fully rescued the Fmr1 KO mice learning and memory deficit to a similar extent of the WT mice levels. Furthermore, a significant improvement in memory in the Fmr1 KO mice treated with 150 mg/kg of metadoxine was found in behavioral tests, such as the T-maze, showing significant improvement in cognitive outcomes. These findings were supplemented by an improved social interaction of KO mice treated with 150 mg/kg of metadoxine. Importantly, improved cognitive executive function, working memory and social interaction following treatment with metadoxine in a valid mouse model of Fragile X correlates with normalization of biochemical markers reflective of neuronal signaling pathways and oxidative stress.

Fragile X syndrome is the most widespread single-gene cause of autism and inherited cause of mental retardation among boys. Anyone with the FMR1 gene mutation can pass it to their children. Approximately 1 in 4,000 males and 1 in 8,000 females have Fragile X syndrome, according to Centers for Disease Control and Prevention (CDC). Not everyone with the mutation will show signs or symptoms of Fragile X, and disabilities will range from mild to severe as well as physical characteristics such as an elongated face, large or protruding ears, large testes (macroorchidism), and behavioral characteristics such as stereotypic movements (e.g. hand-flapping), and social anxiety. Fragile X results from a change or mutation in the Fragile X Mental Retardation 1 (FMR1) gene, which is found on the X chromosome. The gene normally makes a protein called Fragile X Mental Retardation Protein, or FMRP. This protein is important for creating and maintaining connections between cells in the brain and nervous system. The mutation causes the body to make only a little bit or none of the protein, which often causes the symptoms of Fragile X.

Fragile X Syndrome (FXS) often occurs with other conditions such autism spectrum disorders. Autism spectrum disorders (ASDs) are a group of developmental disabilities that can cause significant social, communication and behavior challenges. People with ASDs handle information in their brain differently than other people.

ASDs are "spectrum disorders." That means ASDs affect each person in different ways, and can range from very mild to severe. People with ASDs share some similar symptoms, such as problems with social interaction. But there are differences in when the symptoms start, how severe they are, and the exact nature of the symptoms. ASDs include Autistic Disorder (also called "classic" autism), Asperger Syndrome and Pervasive Developmental Disorder.

Currently, the Food and Drug Administration (FDA) has not approved any drugs specifically for the treatment of Fragile X or its symptoms. There are medications used off label to treat certain symptoms of Fragile X syndrome, however, results vary greatly by patient and some of these medications carry serious risks, may make symptoms worse at first, or take several weeks to become effective. The present invention provides an unmet need for drugs to treat Fragile X or its symptoms.

Accordingly, the invention provides methods of treating, preventing or alleviating a sign or symptom of Fragile X Syndrome and/or autism spectrum disorders by administering to a subject a composition comprising metadoxine.

In general, the signs and symptoms of Fragile X fall into five categories: intelligence and learning; physical, social and emotional, speech and language and sensory disorders commonly associated or sharing features with Fragile X. include for example. Individuals with Fragile X have impaired intellectual functioning, social anxiety, language difficulties and sensitivity to certain sensations. Treatment with metadoxine improves learning and increases sociability in subjects with Fragile X Syndrome.

Autism spectrum disorders are commonly associated with individuals with Fragile X syndrome. Signs and symptoms of autism include significant language delays, social and communication challenges, and unusual behaviors and interests. Many people with autistic disorder also have intellectual disability. Individuals with Asperger syndrome usually have some milder symptoms of autistic disorder. For example, they may have social challenges and unusual behaviors and interests. Individuals with Pervasive Developmental Disorder (PDD-NOS) People meet some of the criteria for autistic disorder or Asperger syndrome, but not all, may be diagnosed with PDD-NOS. People with PDD-NOS usually have fewer and milder symptoms than those with autistic disorder. The symptoms might cause only social and communication challenges.

Treatment with Metadoxine Improves Symptoms of Autism.

Metadoxine is an ion-pair between pyrrolidone carboxylate (PCA) and pyridoxine (vitamin B6) with the two compounds linked in a single product by salification. The pairing with PCA synergistically increases the pharmacological activity of pyridoxine (see, e.g., U.S. Pat. No. 4,313,952). Metadoxine is freely soluble in water and in gastric fluid. Oral absorption of the drug is fast with high bioavailability (60-80%). The half-life of metadoxine in human serum is short (40-60 minutes) without appreciable differences between oral and intravenous administration (Addolorato et al., supra; Lu Yuan et al., *Chin. Med.* 1 2007 120(2) 160-168).

Metadoxine is marketed in several countries as a prescription drug in the form of 500 mg tablets and 300 mg injections. Tablets contain 500 mg of metadoxine, microcrystalline cellulose and magnesium stearate. Ampoules contain 300 mg of metadoxine, sodium metabisulfite, EDTA sodium, methyl-p-hydroxybenzoate and water.

In certain embodiments, metadoxine compositions of the invention, e.g., formulated in whole or in part for sustained or controlled release, enable more efficient use of metadoxine in the treatment, prevention and/or alleviation of a sign or symptom of Fragile X syndrome and conditions/disorders related thereto, such as autism spectrum disorders.

In certain of the above described methods of the invention, the metadoxine or acceptable derivative thereof may be formulated for immediate release upon administration to the subject. In certain of the above described methods of the invention, the metadoxine or acceptable derivative thereof may be formulated for sustained and/or controlled release, and may optionally be formulated to have both immediate release and sustained and/or controlled release characteristics upon administration to the subject. In certain embodiments, metadoxine or a physiologically acceptable derivative thereof is formulated for non-chronic administration. Metadoxine formulations useful in the methods of the present invention described in more detail below.

In certain embodiments, the present invention provides a composition comprising metadoxine or a derivative thereof formulated for sustained and/or controlled release when administered to a subject for improving, treating, preventing and/or alleviating of a sign or symptom of Fragile X syndrome and/or conditions/disorders related thereto, such as autism spectrum disorders.

In certain embodiments, the present invention provides a composition comprising metadoxine or a derivative thereof wherein a portion of the metadoxine or derivative is formulated for sustained and/or controlled release and a portion of the metadoxine or derivative is formulated for immediate release when administered to a subject for improving, treating, preventing and/or alleviating of a sign or symptom of Fragile X syndrome and/or conditions/disorders related thereto, such as autism spectrum disorders.

In certain embodiments, effective serum levels of the active ingredient are achieved within from about 10 to about 20 or 30 or 40 or 50 or 60, 90 minutes, 2 h, 3 h, 4 h, 5 h, 6 h, 7 h, 8 h, 9 h, 10 h following metadoxine or metadoxine derivative administration. In certain embodiments, effective serum levels of the active ingredient in said subject are achieved within from about 5 to about 20 or 30 or 40 or 50 or 60, 90 minutes, 2 h, 3 h, 4 h, 5 h, 6 h, 7 h, 8 h, 9 h, 10 h following metadoxine or metadoxine derivative administration. In certain embodiments, effective serum levels of the active ingredient are achieved within from about 20 to about 20 or 30 or 40 or 50 or 60, 90 minutes, 2 h, 3 h, 4 h, 5 h, 6 h, 7 h, 8 h, 9 h, 10 h following metadoxine or metadoxine derivative administration. In certain embodiments, effective serum levels of the active ingredient are achieved within about 5, 10, 15, 20, 30, 40, 50 or 60, 90 minutes, 2 h, 3 h, 4 h, 5 h, 6 h, 7 h, 8 h, 9 h, 10 h.

The present inventors have developed innovative approaches for the administration of metadoxine or metadoxine derivative based on enteral (via the digestive tract) and/or parenteral (other routes than digestive tract) routes (W02009/004629, the contents of which are incorporated by reference in its entirety). These approaches provide for a rational design of delivery systems with desired properties based on the meticulous selection of the carrier, e.g. appropriate surfactants/co-surfactants composition or micro/nano particles (such as liposomes or nano-liposomes) entrapping the active ingredients, or other additives or excipients, for the delivery system of interest. The enteral delivery systems may be designed for oral administration (tablets, sachets, lozenges, capsules, gelcaps, drops, or other palatable form) or rectal administration (suppository or (mini) enema form). In addition, the delivery system of interest may be in liquid form, for example a drop solution, syrup. Furthermore, the delivery system of interest may be in form of a beverage or food article. Thus, the active ingredient/s used by the invention may be comprised in a beverage, particularly soft drinks like juices, nectars, water, sparkling water and other sparkling drinks, shakes, milk shakes and other milk-based drinks, and the like. Liquid preparations may also be in the form of concentrated syrups, for diluting with water or sparkling water. Alternatively, the active ingredient/s may be comprised in food articles, such as snack bars, health bars, biscuits, cookies, sweets, confectionery products, ice creams, ice lollies, and the like.

Still further, the delivery system may be a food or beverage article comprising a physiologically active pyridoxine derivative, particularly pyridoxol L,2-pyrrolidon-5 carboxylate (metadoxine). In certain embodiments, consumption of the food or beverage article of the invention may lead to achievement of serum levels of the active ingredient within from about 10 to about 40-60 minutes following consumption thereof Examples may be sweets, chocolate, candies and candy bars, energy bars, ice creams, pastry products and the like.

The parenteral ways of administration include subcutaneous, transferal (diffusion through the intact skin), transmucosal (diffusion through a mucous membrane), sublingual, buccal (absorbed through cheek near gumline) administration, or administration by inhalation. In certain embodiments, the compositions used by the invention are not administered by invasive modes of treatment (i.e., are non-invasive). In certain embodiments, the metadoxine or metadoxine derivative compositions are not administered by intravenous injection.

In certain embodiments, compositions used by the invention are delivered as a microcrystalline powder or a solution suitable for nebulization; for intravaginal or intrarectal administration, pessaries, suppositories, creams or foams. A preferred formulation is a formulation for oral administration. Another preferred formulation is for topical administration. Another preferred formulation is for transmucosal administration, sublingual, buccal (absorbed through cheek near gumline) administration, administration by inhalation or ocular administration, e.g., in eye drops.

Administration of metadoxine or metadoxine derivative for medical uses requires safe and efficient delivery systems. The present invention provides delivery systems for safe delivery of a variety of substances due to their special physico-chemical features, particularly direct absorption, by non-invasive means, and consequent avoidance of side effects. The delivery systems significantly enhance efficiency and quality of metadoxine or metadoxine derivative absorption based on its unique physicochemical features, which enables lower concentrations or amounts of active substance to be delivered to a subject in a biologically active form. The delivery systems of the invention provide for the direct access of the active substance to the tissues and thus provide immediate or near-immediate effects of metadoxine or metadoxine derivative to the treated subject. Accordingly, in certain embodiments, the present invention uses a non-invasive pharmaceutical delivery system for the improved administration of a physiologically active pyridoxine, particularly pyridoxol L,2-pyrrolidon-5 carboxylate (metadoxine), or a physiologically acceptable derivative thereof, comprising as the active ingredient said physiologically active pyridoxine in a suitable carrier. In certain embodiments, serum levels of the active ingredient are achieved within from about 10 to about 40-60 minutes following administration. In another embodiment, the invention employs a non-invasive pharmaceutical delivery system for the improved administration of a physiologically active pyridoxine derivative, particularly pyridoxol L,2-pyrrolidon-5 carboxylate (metadoxine), for use in improvement of cognitive behavior in a subject in need thereof, comprising as the active ingredient said pyridoxine derivative, in a suitable carrier. In certain embodiments, serum levels of said active ingredient are achieved within from about 10 to about 40-60 minutes following administration.

In certain embodiments, the drug delivery systems employed by the invention may be designed for oral, nasal, ocular, rectal, subcutaneous, transferal, transmucosal, sublingual, buccal or inhalation administration. The drug delivery systems may provide the active substance in a controlled release mode. In certain embodiments, the drug delivery systems of the invention may further comprise at least one additional pharmaceutically active agent. The delivery systems used by the invention may generally comprise a buffering agent, an agent that adjusts the osmolarity thereof, and optionally, one or more pharmaceutically acceptable carriers, excipients and/or additives as known in the art. Supplementary pharmaceutically acceptable active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. As used herein "pharmaceutically acceptable carrier" includes any and all solvents, dispersion media, coatings, antibacterial and antifungal agents and the like. The use of such media and agents for pharmaceutically active substances is well known in the art. Except as any conventional media or agent is incompatible with the active ingredient, its use in the therapeutic composition is contemplated. It is contemplated that the active agent can be delivered by any pharmaceutically acceptable route and in any pharmaceutically acceptable dosage form. Oral forms include, but are not limited to, tablets, capsules, pills, sachets, lozenges, drops, powders, granules, elixirs, tinctures, suspensions, syrups, and emulsions. Also included are oral rapid-release, time controlled-release, and delayed-release pharmaceutical dosage forms. The active drug components can be administered in a single dosage form or in separate dosage forms to be administered together or independently. The active drug components can be administered in a mixture with suitable pharmaceutical diluents, excipients or carriers (collectively referred to herein as "carrier"), materials suitably selected with respect to the intended form of administration. Where the delivery system is for oral administration and is in the form of a tablet or capsule or the like, the active drug components can be combined with a non-toxic pharmaceutically acceptable inert carrier such as lactose, starch, sucrose, glucose, modified sugars, modified starches, methylcellulose and its derivatives, dicalcium phosphate, calcium sulfate, mannitol, sorbitol, and other reducing and non-reducing sugars, magnesium stearate, stearic acid, sodium stearyl fumarate, glyceryl behenate, calcium stearate and the like. For oral administration in liquid form, the active drug components can be combined with non-toxic pharmaceutically acceptable inert carriers such as ethanol, glycerol, water and the like. When desired or required, suitable binders, lubricants, disintegrating agents and coloring and flavoring agents can also be incorporated into the mixture. Stabilizing agents such as antioxidants, propyl gallate, sodium ascorbate, citric acid, calcium metabisulphite, hydroquinone, and 7-hydroxycoumarin can also be added to stabilize the dosage forms. Other suitable compounds can include gelatin, sweeteners, natural and synthetic gums such as acacia, tragacanth, or alginates, carboxymethylcellulose, polyethylene, glycol, waxes and the like.

Additional suitable pharmaceutically acceptable carriers that may be used in these pharmaceutical compositions include, but are not limited to, ion exchangers, alumina, aluminum stearate, magnesium stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. In some embodiments, the pharmaceutically acceptable carrier is magnesium stearate. Additional pharmaceutical excipients commonly accepted and used are found in, for example, Remington's Pharmaceutical Sciences (Gennaro, A., ed., Mack Pub., 1990).

For purposes of parenteral administration, solutions in suitable oil such as sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art. Methods of preparing various pharmaceutical compositions with a certain amount of active ingredient are known, or will be apparent in light of this disclosure, to those skilled in this art. The half-life of metadoxine in human serum is very short. Lu Yuan et al. (*Chin. Med. J* 2007 120(2) 160-168), showed a mean half life of about 0.8 hour. A way of prolonging serum levels of active moiety is by administering the material in a sustained-release formulation. Because metadoxine is freely soluble in water and in various biological fluids, it is difficult to sustain its release and prolong its absorption time. Therefore, it was unexpected that sustained release could be achieved. A control release dosage form of metadoxine or metadoxine derivative may be based on a predetermined gradual release of the active ingredient in the biological fluids, resulting in a sustained action with small fluctuations of the plasma level over a prolonged period of time.

In certain embodiments, the delivery system used by this invention may be administered in controlled release formulations. In certain embodiments, the method of administration will be determined by the attending physician or other person skilled in the art after an evaluation of the subject's condition and requirements. An embodiment of the method of the present invention is to administer the therapeutic compound described herein in a sustained release form. Any controlled or sustained release method known to those of ordinary skill in the art may be used with the compositions and methods of the invention such as those described in Langer, *Science* 249(4976):1527-33 (1990). Such method comprises administering a sustained-release composition, a suppository, or a coated implantable medical device so that a therapeutically effective dose of the composition of the invention is continuously delivered to a subject of such a method. Sustained release may also be achieved using a patch designed and formulated for the purpose. The composition of the invention may be delivered via a capsule which allows sustained-release of the agent over a period of time. Controlled or sustained-release compositions include formulation in lipophilic depots (e.g., fatty acids, waxes, oils). Also comprehended by the invention are particulate compositions coated with polymers (e.g., poloxamers or poloxamines). Sustained release formulae or devices, or any topical formulations, may additionally contain compositions to stabilize the composition or permeate physiological barrier such as skin or mucous membrane. Exemplary additional components may include any physiologically acceptable detergent or solvent such as, for example, dimethylsulfoxide (DMSO).

In all embodiments of the invention, methods and uses of the invention may employ a composition comprising a salt adduct as defined by the invention formulated as a single dose. Said single dose formulation may be an immediate release formulation, a burst formulation, a prolonged release formulation, a sustained release formulation or any other controlled release formulation known to a person skilled in the art.

In other embodiments of the methods and uses of the invention, a composition comprising a salt adduct defined by the invention may be a combined dosage formulation, wherein different types of formulations are administered to a subject, i.e. any combination of an immediate release formulation, a burst formulation, a prolonged release formulation, a sustained release formulation or any other controlled release formulation known to a person skilled in the art, given either in a single dose or in separate doses given separately, concomitantly or sequentially wherein the gap of time between administration of separate dosages is defined based on the condition and severity of disease or disorder of a subject or the physical condition of said subject.

In some embodiments a composition used by the methods of the invention are formulated as combined dosage forms, wherein at least one dosage from of a suit adduct defined by the invention is in an immediate release form and at least one dosage form of a salt adduct defined by the invention (being the same or different from the salt adduct formulated in the immediate release formulation) is formulated as a controlled (slow and/or sustained) release formulation. In other embodiments the weight ratio of a salt adduct as defined by the invention comprised in said at least one immediate release formulation and at least one controlled release formulation may be 1:1, 1:2, 2:1, 3:2, 2:3, 1:3, 3:1, 4:1, 1:4, 5:2, 2:5, 1:5, 5:1. When employing such combined dosage forms in a method or use of the invention, said at least one immediate release form and at least one controlled release form of a salt adduct defined above, may be administered to a subject separately, concomitantly, sequentially, concurrently, consecutively and so forth. In some embodiments said at least one immediate release form is administered initially. In other embodiments said at least one controlled release formulation is administered initially.

In certain embodiments, the metadoxine or metadoxine derivative in compositions of the invention may be formulated for sustained or controlled release over a period of at least 0.5, 1, 2, 3, 4, 5, 6, 7, 8, 9, 10, 11 or 12 hours. In certain embodiments, the metadoxine or metadoxine derivative in compositions used by the invention may be formulated for sustained or controlled release over a period of about 0.5, 1, 2, 3, 4, 5, 6, 7, 8, 9, 10, 11 or 12 hours. In certain embodiments, the metadoxine or metadoxine derivative in compositions used by the invention may be formulated for sustained or controlled release over a period of between about 0.5 or 1 or 2 or 3 or 4 hours and about 5, 6, 7, 8, 9, 10, 11 or 12 hours. In certain embodiments, the metadoxine or metadoxine derivative in compositions used by the invention may be formulated for sustained or controlled release over a period of between about 5 or 6 or 7 or 8 hours and about 9, 10, 11 or 12 hours.

In certain embodiments, the metadoxine or metadoxine derivative in compositions used by the invention may be in immediate, fast of burst release form.

In certain embodiments, the metadoxine or metadoxine derivative in compositions used by the invention may be formulated to release up to 5, 10, 15, 20, 25, 30, 35, 40, 45, 50, 55, 60, 65, 70, 75, 80, 85, 90, 95, 99, 99.5 or 100% of the total metadoxine or metadoxine derivative in about 0.5, 1, 2, 3, 4, 5, 6, 7 or 8 hours. In certain embodiments, the metadoxine or metadoxine derivative in compositions used by the invention may be formulated to release not less than 5, 10, 15, 20, 25, 30, 35, 40, 45, 50, 55, 60, 65, 70, 75, 80, 85, 90, 95, 99, 99.5 or 100% of the total metadoxine or metadoxine derivative in about 0.5, 1, 2, 3, 4, 5, 6, 7 or 8 hours.

In certain embodiments, the metadoxine or metadoxine derivative in compositions used by the invention may be in a combination of sustained or slow release and immediate or fast release forms. In certain embodiments, the relative proportion of sustained or slow release metadoxine or metadoxine derivative to immediate or fast release metadoxine or metadoxine derivative is, e.g., 1 to 99, 5 to 95, 10 to 90, 15 to 85, 20 to 80, 25 to 75, 30 to 70, 35 to 65, 40 to 60, 45 to 55, 50 to 50, 55 to 45, 60 to 40, 65 to 35, 70 to 30, 75 to 25, 80 to 20, 85 to 15, 90 to 10, 95 to 5, or 99 to 1.

In certain embodiments, a polymeric material is used to sustain or control the release of metadoxine or metadoxine derivative. In certain embodiments, the type of polymeric material and the amount of which is used, has a strong influence on the rate of release of metadoxine or metadoxine derivative from the product of the present invention. Examples of polymers include both hydrophobic and hydrophilic polymers. Examples of hydrophobic polymers include, but are not limited to, ethyl cellulose and other cellulose derivatives, fats such as glycerol palmitostereate, beeswax, glycowax, castorwax, carnaubawax, glycerol monostereate or stearyl alcohol, hydrophobic polyacrylamide derivatives and hydrophobic methacrylic acid derivatives, as well as mixtures of these polymers. Hydrophilic polymers include, but are not limited to, hydrophilic cellulose derivatives such as methyl cellulose, hydroxypropylmethyl cellulose, hydroxyethylcellulose, hydroxypropyl cellulose, carboxymethyl cellulose, sodium carboxymethylcellulose and hydroxyethyl methyl-cellulose polyvinyl alcohol, polyethylene, polypropylene, polystyrene, polyacrylamide, ethylene vinyl acetate copolymer, polyacrylate, poly-urethane, polyvinylpyrrolidone, polymethylmethacrylate, polyvinyl acetate, polyhydroxyethyl methacrylate, as well as mixtures of these polymers. Furthermore, any mixture of one or more hydrophobic polymer and one or more hydrophilic polymer could optionally be used.

In certain embodiments, a polymeric material to be used in compositions of or used by the invention is microcrystalline cellulose such as "AVICEL PH 101" manufactured by FMC BioPolymer's.

In certain embodiments, a polymeric material to be used in compositions of or used by the invention is hydroxypropyl methyl-cellulose such as "METHOLOSE", produced by Shin-Etsu Chemical Co.

In certain embodiments, a polymeric material to be used in compositions of or used by the invention is ethyl cellulose such as "ETHOCEL™", manufactured by The Dow Chemical Company.

In certain embodiments, a polymeric material to be used in compositions of or used by the invention is an acrylic polymer such as "EUDRAGIT RS™", produced by Rohm GmbH.

In certain embodiments, a polymeric material to be used in compositions of or used by the invention is a colloidal silicone dioxide such as "AEROSIL™", manufactured by Degussa.

In certain embodiments, a polymeric material to be used in compositions of or used by the invention is a poly(vinyl acetate) such as "KOLLICOAT SR", manufactured by BASF.

In certain embodiments, a polymeric material to be used in compositions of or used by the invention is an ethyl acetate and vinyl acetate solution such as "DURO-TAK", manufactured by Delasco Dermatologic Lab & Supply, Inc.

In certain embodiments, the compositions of or used by the invention comprise or consist essentially of about 50, 100, 150, 200, 250, 300, 400, 500, 600, 700, 800, or 900 mg to about 1000, 1500, 2000, 2500 or 3000 mg metadoxine or metadoxine derivative. In certain embodiments, the compositions of or used by the invention comprise or consist essentially of about 5, 100, 500, or 1000 mg to about 2000, 4000, 10,000, 15,000, or 20,000 mg AVICEL PH 101™. In certain embodiments, the compositions of or used by the invention comprise or consist essentially of about 25, 50, 100, 150, 200, 250, 300, 350, 400, 450, 500, 550 or 600 mg to about 650, 700, 750, 800, 850, 900, 950, 1000, 5000, 10,000, 15,000 or 20,000 mg of a polymeric material. In certain embodiments, the polymeric material is METHOLOSE, ETHOCEL E10™ or EUDRAGIT RS™. In certain embodiments, METHOLOSE comprises or consists essentially of between 1 and 90% of the formulation, preferably between 5 and 70%. In certain embodiments, ETHOCEL™ comprises or consists essentially of between 1 and 30% of the formulation, preferably between 2 and 20%. In certain embodiments, EUDRAGIT™ comprises or consists essentially of between 1 and 90% of the formulation, preferably between 5 and 70%.

In certain embodiments, delivery systems of or used by the invention comprise delivery devices. In certain embodiments, the compositions of or used by the invention are delivered by an osmotic process at a controlled rate such as by an osmotic pump. The system may be constructed by coating an osmotically active agent with a rate controlling semipermeable membrane. This membrane may contain an orifice of critical size through which agent is delivered. The dosage form after coming into contact with aqueous fluids, imbibes water at a rate determined by the fluid permeability of the membrane and osmotic pressure of the core formulation. This osmotic imbibition of water results in formation of a saturated solution of active material within the core, which is dispensed at controlled rate from the delivery orifice in the membrane.

In certain embodiments, the compositions of or used by the invention are delivered using biodegradable microparticles. In certain embodiments, the system to prepare microparticles consists of an organic phase comprised of a volatile solvent with dissolved polymer and the material to be encapsulated, emulsified in an aqueous phase. In certain embodiments, the biodegradable polymers that can be used for the microparticle matrix, comprises polylactic acid (PLA) or the copolymer of lactic and glycolic acid (PLAGA). The PLAGA polymer degrades hydrolytically over time to its monomeric components, which are readily removed from the body through natural metabolism The preparation of or used by the present invention may also contain an absorption enhancer and other optional components. Examples of absorption enhancers include, but are not limited to, cyclodextrins, phospholipids, chitosan, DMSO, Tween, Brij, glycocholate, saponin, fusidate and energy based enhancing absorption equipment.

Optional components present in the dosage forms include, but are not limited to, diluents, binders, lubricants, surfactants, coloring agents, flavors, buffering agents, preservatives, stabilizing agents and the like.

Diluents, also termed "fillers" include, for example, dicalcium phosphate dihydrate, calcium sulfate, lactose, cellulose, kaolin, mannitol, sodium chloride, dry starch, hydrolyzed starches, silicon dioxide, colloidal silica, titanium oxide, alumina, talc, microcrystalline cellulose, and powdered sugar. For administration in liquid form, the diluents include, for example, ethanol, sorbitol, glycerol, water and the like.

Binders are used to impart cohesive qualities to the formulation. Suitable binder materials include, but are not limited to, starch (including corn starch and pregelatinzed starch), gelatin, sugars (including sucrose, glucose, dextrose, lactose and sorbitol), polyethylene glycol, waxes, natural and synthetic gums, e.g., acacia, tragacanth, sodium alginate, celluloses, and Veegum, and synthetic polymers such as polymethacrylates and polyvinylpyrrolidone.

Lubricants are used to facilitate manufacture; examples of suitable lubricants include, for example, magnesium stearate, calcium stearate, stearic acid, glyceryl behenate, and polyethylene glycol.

Surfactants may be anionic, cationic, amphoteric or nonionic surface active agents, with anionic surfactants preferred. Suitable anionic surfactants include, but are not limited to, those containing carboxylate, sulfonate and sulfate ions, associated with cations such as sodium, potassium and ammonium ions. Particularly preferred surfactants include, but are not limited to long alkyl chain sulfonates and alkyl aryl sulfonates such as sodium dodecylbenzene sulfonate; dialkyl sodium sulfosuccinates, such as sodium bis-(2-ethylhexyl)-sulfosuccinate; and alkyl sulfates such as sodium lauryl sulfate.

Stabilizing agents such as antioxidants, include, but are not limited to, propyl gallate, sodium ascorbate, citric acid, calcium metabisulphite, hydroquinone, and 7-hydroxycoumarin.

If desired, the compositions of or used by the invention may also contain minor amounts of nontoxic auxiliary substances such as wetting or emulsifying agents, preservatives, and the like.

Any of the compositions of or used by the invention may be used alone or in combination with one or more additional therapeutic agents, for the improvement of cognitive behavior. Examples of additional therapeutic agents are: amphetamines, methylphenidate HCl, dexmethylphenidate hydrochloride, atomoxetine, reboxetine, fluoxatine, sertraline, paroxetine, fluoroxamine, citalopram, venlafaxine, bupropion, nefazodone and mirtazapine.

The amount of both the compound and the additional therapeutic agent that may be combined with the carrier materials to produce a single dosage form will vary depending upon the host treated and the particular mode of administration. Preferably, the compositions of this invention should be formulated so that a dosage of between 0.1-1 g/kg body weight/day, preferably 0.1-300 mg/kg body weight, can be administered. The dose of the compound depends on the condition and the illness of the patient, and the desired daily dose. In human therapy, the oral daily dose is 10-3000 mg or preferably 100-3000 mg. For example the daily dose is 10, 25, 50 100, 150, 200, 250, 300, 350, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, or 3000 mg. These doses are administered in unit dosage forms, which may be administered in a single daily dose or divided into 2-3 smaller doses for each day in certain cases.

In certain embodiments, the compositions of the present invention may act synergistically in combination with each other and may further act synergistically in the presence of an additional therapeutic agent. Therefore, the amount of compound(s) and additional therapeutic agent(s) in such compositions will be less than that required in a monotherapy utilizing only that therapeutic agent. In such compositions a dosage of between 0.1-1 g/kg bodyweight/day of the additional therapeutic agent can be administered.

Definitions

For convenience, certain terms employed in the specification, examples, and appended embodiments, are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including by not limited to"

The term "or" is used herein to mean, and is used interchangeably with, the term "and/or," unless context clearly indicates otherwise.

The term "such as" is used herein to mean, and is used interchangeably, with the phrase "such as but not limited to".

The term "prophylactic" or "therapeutic" treatment refers to administration to a subject of one or more of the compositions of the invention. If it is administered prior to clinical manifestation of the unwanted condition (e.g., clinical or other unwanted state of the host animal) then the treatment is prophylactic, i.e., it contributes to prevention of, i.e., protection of the subject against developing an unwanted condition, whereas if administered after manifestation of an unwanted condition, the treatment is therapeutic (i.e., it is intended to diminish, ameliorate or prevent progression of the unwanted condition or side effects there from).

The term "therapeutic effect" refers to a local or systemic effect in animals, particularly mammals, and more particularly humans, caused by a pharmacologically active substance or substances. The term thus means any substance intended for use in diagnosis, cure, mitigation, treatment or prevention of disease or in the enhancement of desirable physical or mental development and conditions in an animal or human. The term "therapeutically effective amount" means that amount of such a substance that produces some desired local or systemic effect at a reasonable benefit/risk ratio applicable to any treatment. In certain embodiments, a therapeutically-effective amount of a compound or composition will depend on its therapeutic index, solubility, and the like. For example, certain metadoxine or metadoxine derivatives formulations of the present invention may be administered in a sufficient amount to produce a reasonable benefit/risk ratio applicable to a selected treatment, as may be determined by the skilled artisan.

The term "effective amount" refers to the amount of a therapeutic reagent that when administered to a subject in an appropriate dose and regimen produces at least one desired result.

A "subject" or "patient" to be treated by a method of the invention may mean either a human or non-human animal, preferably a mammal. The term "subject" as used herein may refer to a healthy individual, or a subject suffering Fragile X Syndrome or Autism Spectrum Disorder. In alternative embodiments, the terms "subject" and "healthy subject" and "subject in need" and "patient in need" as used herein exclude subjects under alcohol influence following alcohol consumption of any form, alcoholics (alcohol addicts), and abstinent alcoholics.

As used herein the term "salt adduct" is meant to encompass a salt product of a direct addition of two or more distinct ions, wherein the overall charge of the salt adduct is zero. In certain embodiments, the salt adduct comprises one positively charged moiety having a single positive charge functional group (i.e., the positively charged moiety is charged with +1 net charge) and one negatively charged moiety having a single negative charge functional group (i.e., the negatively charged moiety is charged with −1 net charge). In certain embodiments, the salt adduct comprises one positively charged moiety having two positively charged functional groups, which may be the same or different (i.e., the positively charged moiety is charged with +2 net charge) and two negatively charged moieties, which may be the same or different, and each having a single negative charged functional group (i.e., each negatively charged moiety is charged with −1 net charge). In certain embodiments, the salt adduct comprises two positively charged moieties, which may be the same or different, having each one positively charged functional group (i.e., each positively charged moiety is charged with +1 net charge) and one negatively charged moiety, having two negatively charged functional groups, being the same or different (i.e., the negatively charged moiety is charged with −2 net charge). In certain embodiments, the salt adduct comprises a positively charged moiety charged with +n net charge (originating from one or more positively charged functional groups, which may be the same or different), and a negatively charge moiety having −n (originating from one or more negatively charged functional groups, which may be the same or different) net charge, wherein n is an integer which may be equal to 1, 2, 3, 4, 5 or 6.

As used herein, a "positively charged moiety of a salt adduct" of the invention is the corresponding acid of pyridoxine, or any derivative thereof In certain embodiments, the positive charge of the positively charged moiety stems from the protonated basic nitrogen atom of pyridoxine (as for example in compound (2)) or any derivative thereof (such as for example compounds of formula (I)). In certain embodiments, the positively charged pyridoxine derivative is substituted with a positively charged functional group such as for example —NH$_3^+$, —CH$_2$NH$_3^+$, NH$_2$R$^+$, —NHR$_2^+$ (wherein each R is independently a C$_1$-C$_6$ alkyl), which may, in some embodiments, be present in addition to the positively charged protonated basic aromatic nitrogen atom in the pyridine ring.

It should be understood that moieties of a salt adduct of the invention may contain each at least one chiral center, and thus may exist in, and be isolated as, any stereoisomer thereof including, enantiomers, diastereomers or any mixtures thereod including, but not limited to racemic mixtures. The present invention includes any possible stereoisomer (e.g. enantiomers, diastereomers), any mixtures thereof including, but not limited to, racemic mixtures, of any of the individual moieties of a salt adduct of the invention. Where the herein-described processes for the preparation of each of the moieties of a salt adduct of the invention give rise to mixtures of stereoisomers, these isomers may be separated by conventional techniques, such as preparative chromatography. The moieties of a salt adduct of the invention may be each prepared in any mixture of possible stereoisomers thereof, including but not limited to racemic mixtures thereof, or individual stereoisomers (e.g. enantiomers, diastereomers) may be prepared either by enantiospecific synthesis or by chiral chromatographic separation of a racemate. Whenever referring to amino acids, the invention should be understood to encompass natural and non-natural amino acids or any derivative thereof Throughout this specification, the word "comprise" or variations such as "comprises" or "comprising" will be understood to imply the inclusion of a stated integer or groups of integers but not the exclusion of any other integer or group of integers.

The term "bio-available" means that at least some amount of a particular compound is present in the systemic circulation. Formal calculations of oral bioavailability are described in terms of an F value ("Fundamentals of Clinical Pharmacokinetics," John G. Wegner, Drug Intelligence Publications; Hamilton, Ill. 1975). F values are derived from the ratio of the concentration of the parent drug in the systemic circulation (e.g., plasma) following intravenous administration to the concentration of the parent drug in the systemic circulation after administration by a non-intravenous route (e.g., oral). Therefore, oral bioavailability within the scope of the present invention contemplates the ratio or F value of the amount of parent drug detectable in the plasma after oral administration compared to intravenous administration.

The term "treating" or "treatment" refers to mitigating, improving, relieving or alleviating at least on symptom of a condition, disease or disorder in a mammal, such as a human, or the improvement of an ascertainable measurement associated with a condition, disease or disorder. Treatment as used herein also encompasses treatment of healthy individuals.

The term "acceptable derivative" with respect to metadoxine or metadoxine derivatives refers to any salt, conjugate, ester, complex or other chemical derivative of metadoxine or any of the moieties comprising the same, which, upon administration to a subject, is capable of providing (directly or indirectly) metadoxine or a metabolite or functional residue thereof, or measurable metadoxine activity. The term "physiologically compatible metadoxine derivative" may be used interchangeably herein with the term "acceptable derivative" and refers to a functional, active, pharmaceutically acceptable derivative of metadoxine.

The term "excipient" refers to an inactive substance used as a carrier for the active ingredient in a formulation.

The term "controlled release" refers to any formulation which delivers an agent at a controlled rate for an extended time and is designed to achieve a desired agent level profile.

The term "sustained release" is used in its conventional sense to refer to a formulation that provides for gradual release of an active material over an extended period of time, which in certain embodiments may also further result in substantially constant blood levels over an extended time period, i.e., controlled release.

The term "immediate release" is used in its conventional sense to refer to a formulation that provides for non delayed or controlled release of an active material upon administration.

The term "half-life" of a substance is the time it takes for a substance to lose half of its pharmacologic, physiologic, or other activity. Biological half-life is an important pharmacokinetic parameter and is usually denoted by the abbreviation tin.

The term "non-invasive" refers to modes of treatment which do not puncture the skin.

The term "non-chronic administration" may be used interchangeably herein with the term "acute administration" and refers to giving a measured or non-measured quantity or portion of a medication to a subject on a non-regular basis. Non-chronic administration may be a single dose treatment or a multiple dose treatment, and may optionally be given over time. Typically but not always, a non-chronic administration is given to treat or prevent a non-chronic condition. Certain chronic conditions may also benefit from non-chronic administration of a metadoxine or metadoxine derivatives composition described herein.

The term "chronic administration" refers to giving a measured quantity of a medication on a regular basis to a subject. In some embodiments, chronic administration is to treat or prevent one or more chronic conditions, problems or diseases. Chronic diseases have one or more of the following characteristics: they are permanent, leave residual disability, are caused by nonreversible pathological alteration, require special training of the patient for rehabilitation, or may be expected to require a long period of supervision, observation, or care.

The term "single dose treatment" refers to giving a measured quantity of a medication to be taken at one time. It is given to treat non-chronic conditions on an irregular basis, depending on personal need.

The term "$t_{max}$" refers to the time to peak concentration. Calculation of time at which maximum concentration occurs after a single dose administration is performed according to the formula:

$$t_{max} = \frac{2.303}{\lambda_\alpha - \lambda_z} \log \frac{\lambda_\alpha}{\lambda_z}$$

Where λα and λz are the apparent absorption and elimination rate constants, respectively.

EXAMPLES

Example 1: General Methods

The examples as described herein were performed using the reagents and methods generally described below.

Experimental Animals

Fmr1 knockout mice (KO2) mice (The Dutch-Belgium Fragile X Consortium, 1994), initially obtained from the Jackson Laboratory, and wild type (WT) littermates were generated on a C57BL/6J background and repeatedly backcrossed onto a C57BL/6J background for more than eight generations. The Fmr1 knockout mice were housed in groups of the same genotype in a temperature and humidity controlled room with a 12-h light-dark cycle (lights on from 7 am to 7 pm; testing was conducted during light phase). Room temperature and humidity were recorded continuously in the holding room while food and water were available ad libitum. Testing was conducted on healthy Fmr1 knockout mice and their wild type littermates (N=10 mice per treatment group) at 2 or 6 months of age during the behavioral experiments. Mice were housed in commercial plastic cages and experiments were conducted in line with the requirements of the UK Animals (Scientific Procedures) Act, 1986. All experiments were conducted with experimenters blind to genotype and drug treatment. Animals were allowed a minimum acclimatization period of one week prior to performing any experiment. No prophylactic or therapeutic treatment was administered during the acclimatization period.

Drugs

For Study 1 (Example 2), metadoxine was dissolved in saline and administered intraperitoneally at doses of 100, 150, or 200 mg/kg/once daily for 7 days. For Study 2 (Example 3), in vivo testing, metadoxine was dissolved in saline and administered at an intraperitoneal dose of 150 mg/kg per day or at an oral dose of 150 or 300 mg/kg/day (in a volume of 0.1 ml) once daily for seven days. For Study 2, in vitro testing, metadoxine was administered at concentration of 300 µM for five hours. In all cases, saline was used as a vehicle (control).

Behavioral Testing

Social Interaction and Social Recognition Memory:

Mice are a social species that engage in easily scored social behaviors including approaching, following, sniffing, grooming, aggressive encounters, sexual interactions, parental behaviors, nesting, and sleeping in a group huddle. Social approach in mice was evaluated by sniffing duration directed to a novel mouse.

Mice were placed in a test arena/cage of the same order of magnitude in size as the adult's home cage (40×23×12 cm cage, with a Perspex lid to facilitate viewing the mice) with fresh wood chippings on the floor. A background mouse odor was created by putting in some non-experimental mice into the apparatus prior to testing. Mice were transferred to the experimental room 10-15 min prior to testing. A test subject and a juvenile were placed simultaneously into the test cage. The total duration and number of bouts of social investigation, defined as sniffing and close following (<2 cm from the tail) of the stimulus juvenile by the tested mouse, was assessed for 3 min. 30 min later, the test was repeated using the same stimulus juvenile. Data parameters collected were the total duration and total number of bouts of sniffing for the acquisition and recognition. A social memory ratio was derived, defined as trial 2/trial 1+2. Therefore, no memory (e.g. 20/(20+20)=0.5 and memory (e.g. 10/(20+10)=<0.5.

Y-Maze Alternation:

Two tasks were implemented. The first was an unlearned assessment of spontaneous alternation between arm entries. The second was a spatial reference memory task in which the animal had to learn which of the two arms was baited with a food reward. The day prior to the start of the training, mice were allowed to freely explore the maze for 5 min. Next, they received two trials, one in which the food was located on the left arm and one in which the food was positioned on the right arm. This procedure prevented the development of a preference for one of the arms.

Y-Maze Water Maze:

A clear Perspex Y-maze was filled with 2 cm of water at 20° C. This motivated the mouse to leave the maze after paddling to an exit tube at the distal end of one arm. The maze was placed in the middle of a room surrounded by prominent visual cues.

Rewarded T Maze Alternation:

An elevated or enclosed apparatus in the form of a T (placed horizontally) was used. Mice were placed at the base of the T and were allowed to choose one of the goal arms abutting the other end of the stem. Two trials were conducted in quick succession, the second trial required mice to choose the arm not visited before, reflecting memory of the first choice (spontaneous alternation). This tendency was reinforced by making the animal hungry and rewarding it with a preferred food if it alternated. Specifically, after a four day habituation period on the T-maze, mice were trained to alternate arm choices to receive sweet condensed milk as reward.

Successive Alleys:

The apparatus consisted of four successive, linearly arranged, increasingly anxiogenic alleys (each succeeding alley was painted a lighter color, had lower walls and/or was narrower than the previous alley) made of painted wood. Each section or alley was 25 cm long. Alley 1 had 25 cm high walls, was 8.5 cm wide, and was painted black. A 0.5 cm step down led to alley 2, which was again 8.5 cm wide, but had 1.3 cm high walls and was grey. A 1.0 cm step down led to alley 3, which was 3.5 cm wide, had 0.8 cm high walls, and was white. A 0.4 cm step led down to alley 4, which was also white, but had 1.2 cm wide and 0.2 cm high walls. The apparatus was elevated by anchoring the back of alley 1 to a stand, 50 cm high. Padding was provided under arms 3 and 4 in case a mouse fell off. Each mouse was placed at the closed end of alley 1 facing the wall. Timers were started 1) for the overall length of the test (5 min)+the latency to enter each arm, and 2) for the time spent in alley 1. When the mouse placed all 4 feet on to the next alley, it was considered to have entered the alley. Total time spent in each alley (all four feet) was recorded.

Contextual Fear Conditioning:

In the fear conditioning experiment, mice were placed into a novel environment (dark chamber) and received pairings of a cue and electric footshock (0.2 mA for 1 sec (Study 1) or 0.7 mA for 0.5 sec (Study 2)). Subsequently, when tested in the original training context, mice displayed a natural defensive response termed freezing (Blanchard, 1969) or contextual fear conditioning. Freezing time was defined as the time that the mice spent in immobile behavior, except for respiration. The data was expressed as the percentage of the test period. 24 hours after a training session, mice were tested for 5 min in the training chamber with no shock presentation and observed for freezing behavior.

Statistics:

Multivariate analysis of variance was employed to assess group differences across data. Repeated measures ANOVA were performed for behavioral data. Statistically significant effects in each ANOVA were followed with post hoc comparisons, using the Newman-Keuls test (Study 1) or the Tukey test (Study 2). A p value of less than 0.05 was considered significant.

Biochemical Testing
Phosphorylated ERK and Akt:
The Ras-Mek-ERK and PI3K-Akt-mToR signaling pathways are involved in mediating activity dependent alterations in gene transcription underlying changes in synaptic plasticity (Klann and Dever, 2004). Phosphorylated ERK and Akt protein expression was measured by western blot analysis as previously described by Lopez Verrilli (Lopez Verrilli et al., 2009). The antibodies employed were anti-phosphospecific antibodies against Akt (1/1000) and kinase (ERK) 1/2 (1/2000) (Cell Signaling Technology, Danvers, Mass., USA). The antibody against phospho-ERK detects phosphorylation at phospho-ERK 1/2 (Thr202/Tyr204) whereas the antibody against phospho-Akt detects phosphorylation at phospho-Akt (Thr308). Total Akt and ERK 1/2 protein content and phosphorylated ERK and Akt were evaluated by blotting membranes with antiphospho-Akt (1/1000) and antiphospho-ERK antibodies (1/2000) (Cell Signaling Technology, Danvers, Mass., USA). Akt or ERK phosphorylation was normalized to protein content in the same sample and expressed as % of change with respect to basal conditions, considering basal levels as 100%. Protein loading was evaluated by stripping and re-blotting membranes with j-actin antibody (1/1000) (Sigma-Aldrich, St. Louis, Mo., USA). Phosphorylated ERK and Akt protein expression in blood lymphocytes was measured by flow cytometry. For lymphocyte biomarker determinations, a FACStar plus (Becton Dickinson) was used with the excitation laser tuned at 488 nm and green fluorescence from FITC (GST) was collected through a 515-545 nm bandpass filter. The mean FITC fluorescence Intensity was calculated in relation to the fluorescence of reference cells. The mean cellular fluorescence intensity (MFI) is directly proportional to the mean number of Ab molecules bound per cell.

Neuronal Morphology:
Hippocampal cell cultures were prepared from wild type and Fmr1 KO fetal mice at embryonic day of gestation 17.5 (E17.5). Mice were killed by cervical dislocation and dissociated hippocampal cells were plated in 15 mm multi well vessels (Falcon Primaria). After 5 d in vitro, green fluorescent protein (GFP) was transfected to facilitate monitoring dendritic spine morphogenesis after drug treatment (Ethell and Yamaguchi, 1999; Ethell et al., 2001, Henkemeyer et al., 2003). Dendritic spines were formed at around 16 days in vitro (DIV). Cultures were treated with metadoxine at 300 μM concentration at day 17 in vitro for 5 hrs.

Filopodia density of GFP transfected neurons was quantified by performing Sholl analyses of stacked Zeiss confocal generated images (40× objective, stack of 20×0.2 μm). With Metamorph software, concentric equally spaced circles (every 20 μm) were drawn around the cell soma of each neuron and subsequently, the amount of filopodia was counted per circle. Averages of counts were compared with unpaired two-tailed Student's T-tests.

Spine maturity of GFP transfected neurons was analyzed with Metamorph software (Molecular Devices, Sunnyvale, Calif.). Two distal dendritic segments of 70 100 μm were chosen per neuron for spine morphometric analysis. For each spine, the length and the width were measured. The length was defined as the distance from the base to the tip of the protrusion; whereas width was defined as the maximum distance perpendicular to the long axis of the spine. Measurements were compared with unpaired two tailed Student's T-tests and ANOVA corrected for multiple comparisons.

De Novo Hippocampal Protein Synthesis:
Transverse hippocampal slices (400 μm) were obtained from 6-week-old Fmr1 knockout and WT mice. A protein synthesis assay was performed as previously described using the nonradioactive fluorescence-activated cell sorting-based assay, surface sensing of translation (SUnSET) method, which allows the monitoring and quantification of global protein synthesis in individual mammalian cells and in heterogeneous cell populations. (Hoeffer, 2011). The concentration of metadoxine used in this study was 300 μM.

Example 2: The Effect of Metadoxine (100 to 200 mg/kg) Treatment on Learning and Memory Deficits and Biochemical Abnormalities in the Fmr1 Knockout Mouse Model of Fragile X Syndrome (Study 1)

Figure 1:
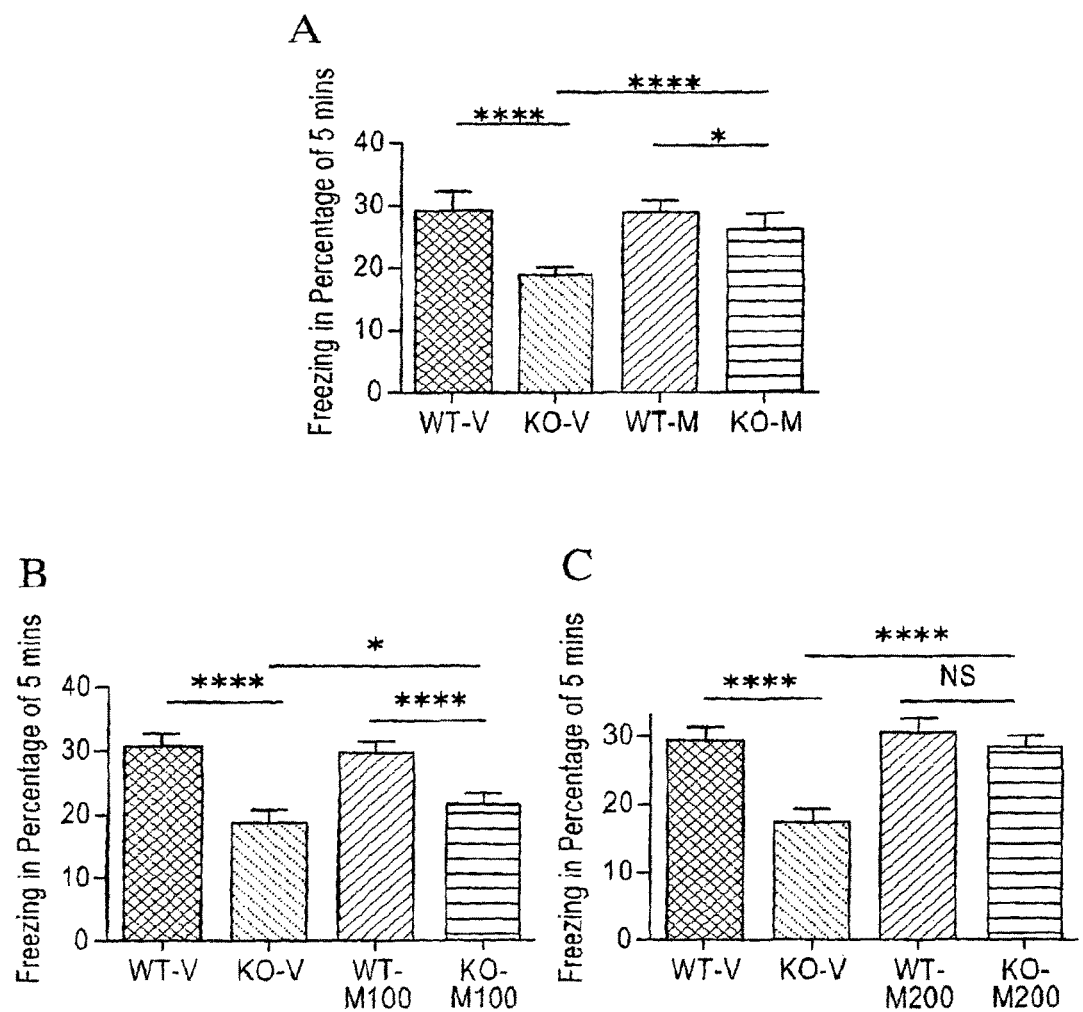
FIG. 1 shows the effect of seven days of once daily intraperitoneal (ip) administration of vehicle (V) or metadoxine (M) (100, 150, or 200 mg/kg) in 2-months old Fmr1 knockout (KO) or Wild Type (WT) mice on contextual fear conditioning. Specifically, Panel A shows the effect of vehicle or 150 mg/kg of metadoxine. Panel B shows the effect of vehicle or 100 mg/kg of metadoxine. Panel C shows the effect of vehicle or 200 mg/kg of metadoxine. Data shown are mean±standard error of the mean (sem), N=10 mice per group. *$p<0.05$, ****$p<0.0001$, and NS=Not Significant.

Behavioral Analyses
Contextual Fear Conditioning:
An initial experiment tested the effect of intraperitoneal administration of vehicle or 150 mg/kg metadoxine once daily for seven days on contextual fear conditioning in groups of N=10 WT and Fmr1 knockout mice. Vehicle-treated Fmr1 knockout mice showed a deficit in learning in the contextual fear conditioning paradigm as reflected in a reduction in freezing during the test session (FIG. 1, Panel A ($p<0.0001$)). Metadoxine administration reversed the learning deficit effect in Fmr1 knockout mice, this reversal being partial such that metadoxine-treated animals differed from the metadoxine-treated WT animals ($p<0.05$). A replication of this experiment investigated the dose-dependent effects of intraperitoneal administration of vehicle, 100, or 200 mg/kg metadoxine once daily for seven days on contextual fear conditioning in groups of N=10 WT and Fmr1 knockout mice (FIG. 1, Panels B and C). In this experiment, vehicle-treated Fmr1 knockout mice showed a learning deficit compared to vehicle-treated WT mice ($p<0.0001$), replicating the first experiment. 100 mg/kg metadoxine produced a reversal of the deficit in Fmr1 knockout mice ($P<0.05$) but this was a partial reversal since metadoxine-treated Fmr1 knockout mice differed from the metadoxine-treated Wild Type mice ($p<0.0001$). The learning deficit seen in Fmr1 knockout mice was completely reversed following treatment with 200 mg/kg i.p. metadoxine (treated Fmr1 mice differed from vehicle-treated Fmr1 knockout mice ($P<0.0001$) but did not differ from metadoxine-treated WT mice). Metadoxine treatment had no effect on WT mice in either experiment (FIG. 1, Panels A-C).

Figure 2:
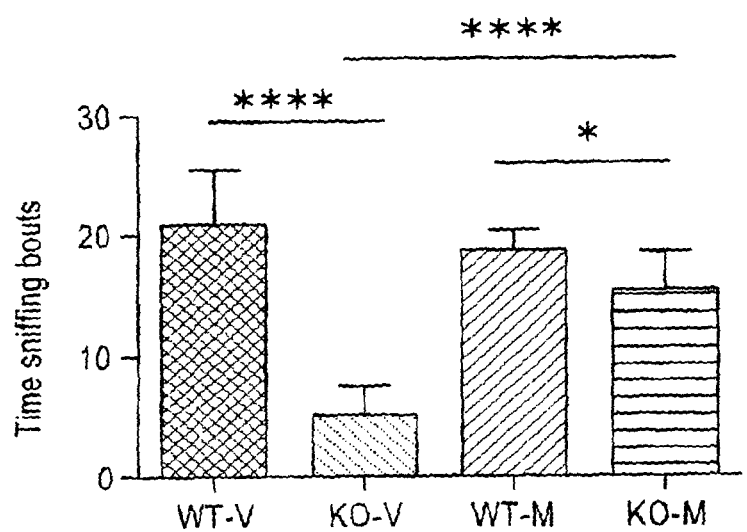
FIG. 2 shows the effect of seven days of once daily intraperitoneal administration of vehicle (V) or 150 mg/kg metadoxine (M) in 2-months old Fmr1 knockout (KO) or Wild Type (WT) mice on social approach behavior. Data shown are mean±sem, N=10 mice per group. *$p<0.05$ and ****$p<0.0001$.

Social Approach:
Vehicle-treated Fmr1 knockout mice showed less social approach as indexed by sniffing bouts (FIG. 2 ($p<0.0001$)). Once daily intraperitoneal treatment with 150 mg/kg metadoxine for seven days increased social approach in Fmr1 knockout mice ($p<0.0001$ compared to vehicle treated Fmr1 knockout mice). Fmr1 knockout mice treated with metadoxine differed from metadoxine-treated WT mice ($p<0.05$), although there was a trend approaching the effect of the WT mice. Metadoxine treatment had no effect on WT mice.

Figure 3:
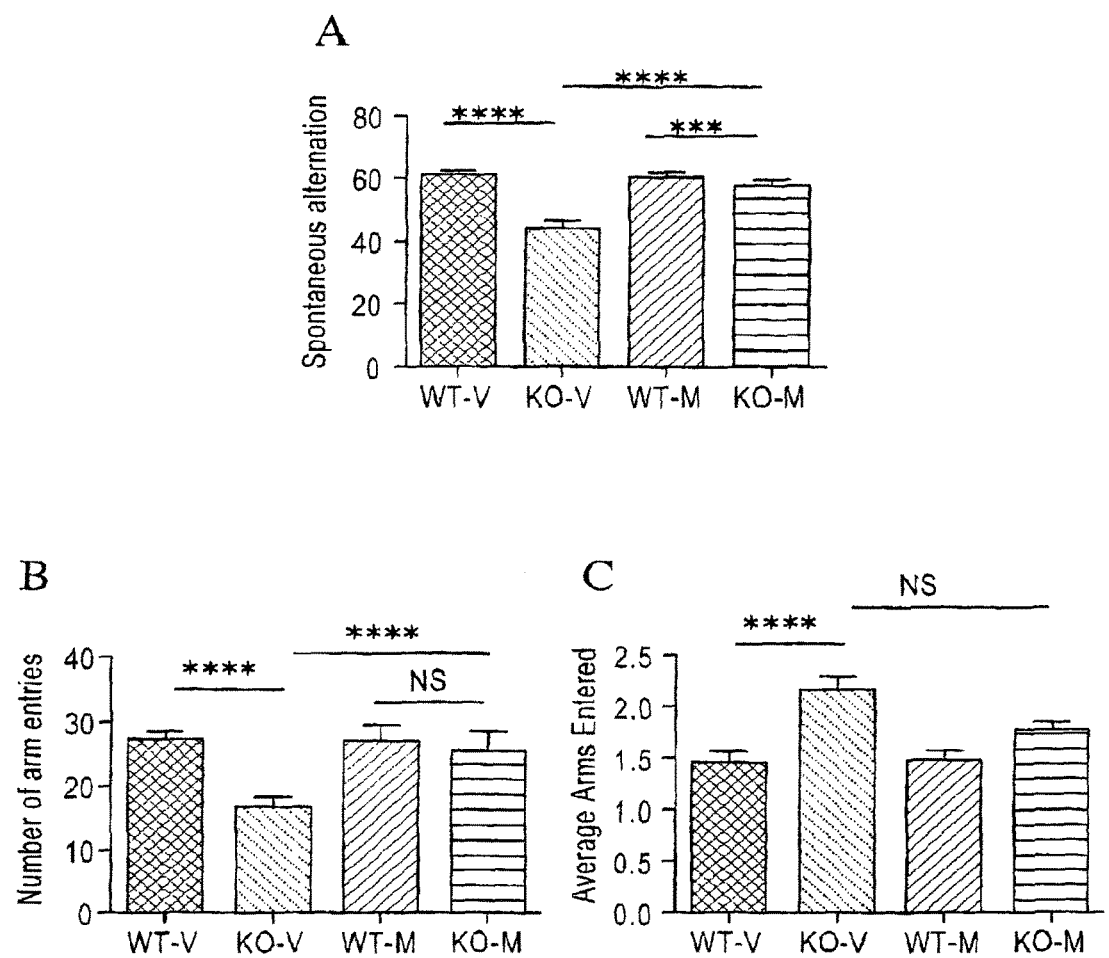
FIG. 3 shows the effect of seven days of once daily intraperitoneal administration of vehicle (V) or 150 mg/kg metadoxine (M) on Y-maze spontaneous alternation (Panel A), Y-maze rewarded alternation (Panel B) or Y-maze water maze spatial discrimination (Panel C) in 2-months old Fmr1 knockout (KO) or Wild Type (WT) mice. Data shown are mean±sem, N=10 mice per group. *$p<0.001$, **$p<0.0001$, and NS=Not Significant.

Y-Maze Spontaneous Alternation:
The effect of seven days of once daily treatment with vehicle or 150 mg/kg metadoxine on spontaneous alternation in groups of N=10 WT or Fmr1 knockout mice is shown in FIG. 3, Panel A. Vehicle-treated Fmr1 knockout mice showed less spontaneous alternation than vehicle treated WT mice ($p<0.0001$). Metadoxine treatment increased spontaneous alternation compared to vehicle treatment in Fmr1 knockout mice ($p<0.0001$), although metadoxine-treated Fmr1 knockout mice showed a deficit compared to metadoxine-treated WT mice (p<0.01). Metadoxine therefore produced a partial reversal of the deficit seen in Fmr1 knockout mice.

Y-Maze Reference Memory Task:

The effect of seven days of once daily treatment with vehicle or 150 mg/kg metadoxine on rewarded reference memory learning in groups of N=10 WT or Fmr1 knockout mice is shown in FIG. 3, Panel B. Vehicle-treated Fmr1 knockout mice made less appropriate arm entries than vehicle-treated WT mice (p<0.0001). Metadoxine treatment reduced this deficit (p<0.0001) compared to vehicle-treated Fmr1 knockout mice, such that metadoxine-treated Fmr1 knockout mice did not differ from metadoxine-treated WT mice.

Metadoxine Treatment Had No Effect on WT Mice.

Y-Maze Water Maze Left Right Discrimination:

The effect of seven days of once daily treatment with vehicle or 150 mg/kg metadoxine on aversively motivated spatial discrimination learning in groups of N=10 WT or Fmr1 knockout mice is shown in FIG. 3, Panel C. Vehicle-treated Fmr1 knockout mice showed a greater number of incorrect arm entries than vehicle-treated WT mice. This deficit was reduced by treatment with metadoxine.

Figure 4:
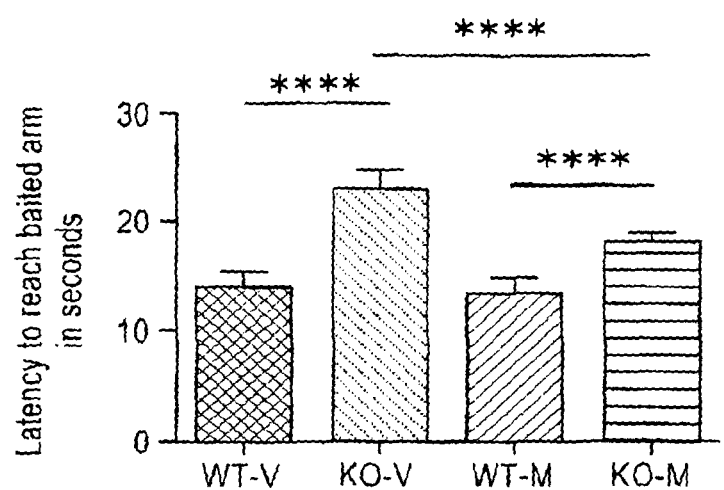
FIG. 4 shows the effect of seven days of once daily intraperitoneal administration of vehicle (V) or 150 mg/kg metadoxine (M) on T-maze rewarded alternation in 2-months old Fmr1 knockout (KO) or Wild Type (WT) mice. Data shown are mean±sem, N=10 mice per group. ****$p<0.0001$.

T-Maze Rewarded Alternation Task:

The effect of seven days of once daily treatment with vehicle or 150 mg/kg metadoxine on rewarded alternation working memory in groups of N=10 WT or Fmr1 knockout mice is shown in FIG. 4. Vehicle-treated Fmr1 knockout mice showed a greater latency to reach the correct arm compared to vehicle-treated WT mice (p<0.0001). Metadoxine treatment reduced this deficit compared to vehicle treatment in Fmr1 knockout mice (p<0.0001), this reversal being partial since metadoxine-treated Fmr1 knockout mice responded more slowly than WT mice (p<0.0001).

Figure 5:
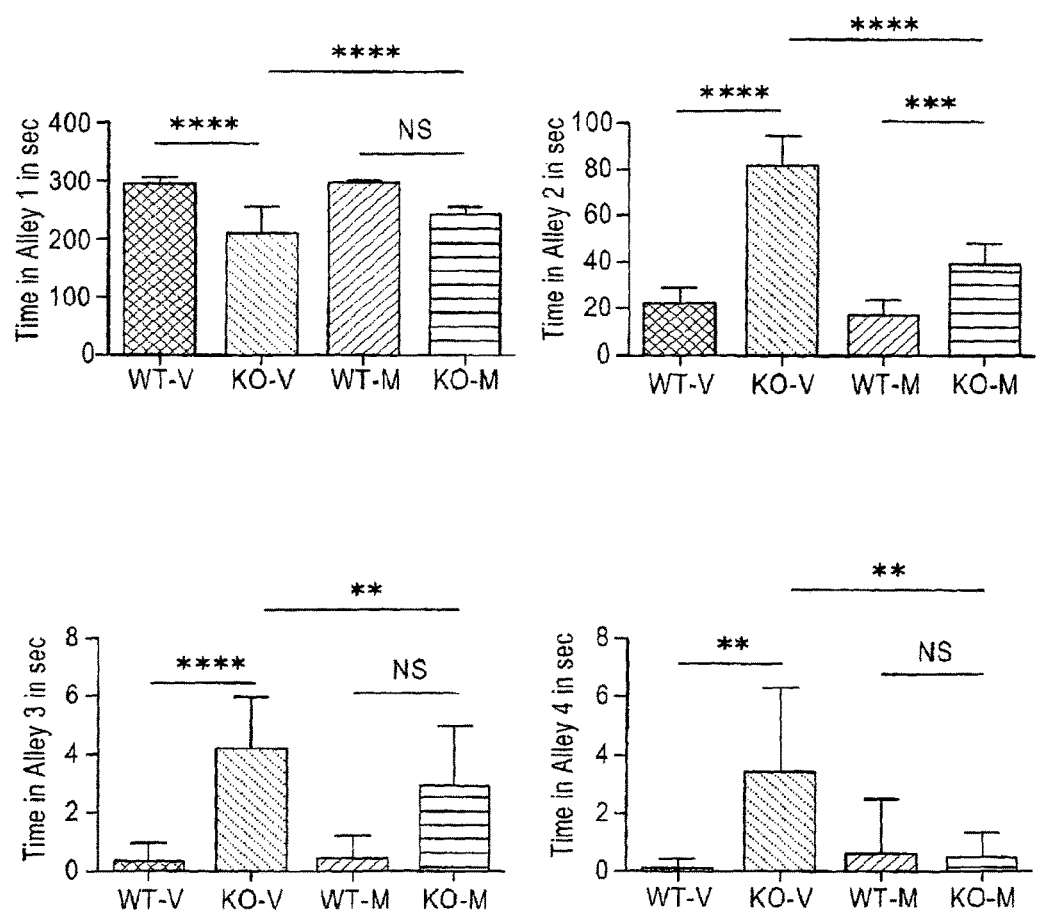
FIG. 5 shows the effect of seven days of once daily treatment with vehicle (V) or 150 mg/kg metadoxine (M) on behavior in the successive alleys task in groups of N=10 Wild Type (WT) or Fmr1 knockout (KO) 2-months old mice. The successive alleys of the apparatus presented progressively more anxiogenic environments to explore mice. Movement down the alleys therefore assessed anxiety. In addition, overall activity levels could also be quantitated in the apparatus.

Successive Alleys:

The effect of seven days of once daily treatment with vehicle or 150 mg/kg metadoxine on behavior in the successive alleys task in groups of N=10 WT or Fmr1 knockout mice is shown in FIG. 5 and further described below.

The successive alleys test effectively measured anxiety (latency to enter the Alley 1) and hyperactivity (Alleys 2 to 4). Progression from Alley 1 through the successive Alleys 2, 3, and 4 was associated with exposure to an increasingly brightly colored environment with increasingly lower walls and narrower, more exposed open arms. Time spent on, and entries into, the open arms indicated anxiety; conversely, increasing time spent in more open arms reflected hyperactivity. These factors allowed for a sensitive test bracketing a range of anxiety-like behaviors together with hyperactivity.

Alley 1:

The Fmr1 knockout mice showed more anxiety than WT mice (p<0.001). Fmr1 knockout mice treated with metadoxine showed an amelioration in anxiety compared with the vehicle treated Fmr1 knockout mice (p<0.001), such that complete normalization occurred. There was no difference between the metadoxine-treated Fnmr1 knockout and metadoxine-treated WT mice. Also, metadoxine treatment had no effect on WT mice.

Alley 2:

WT mice showed less activity in Alley 2 when compared with the Fmr1 knockout mice (p<0.0001). Treatment with metadoxine reduced hyperactivity in the Fmr1 knockout mice (p<0.001), although this reversal of hyperactivity was partial since metadoxine-treated Fmr1 knockout and WT mice differed (p<0.001). Metadoxine treatment had no effect on WT mice.

Alley 3:

Fmr1 knockout mice showed hyperactivity compared to WT mice (p<0.0001). This hyperactivity was not reversed by metadoxine, since metadoxine-treated Fmr1 knockout mice did not differ from vehicle-treated Fmr1 knockout mice. Metadoxine treatment had no effect on WT mice.

Alley 4:

Fmr1 knockout mice showed hyperactivity compared to WT mice (p<0.01). Metadoxine treatment reversed this hyperactivity since metadoxine-treated Fmr1 knockout mice showed less activity than vehicle-treated Fmr1 knockout mice (p<0.01). This effect reflected a normalization since metadoxine-treated Fmr1 knockout mice did not differ from metadoxine-treated WT mice. Metadoxine treatment had no effect on WT mice.

Overall, without wishing to be bound by theory, the successive alleys test showed that Fmr1 knockout mice had increased anxiety and hyperactivity compared to WT mice. Metadoxine treatment reduced this anxiety and hyperactivity in the Fmr1 knockout mice whilst leaving WT mice unaffected.

Biochemical Analyses

Figure 6:
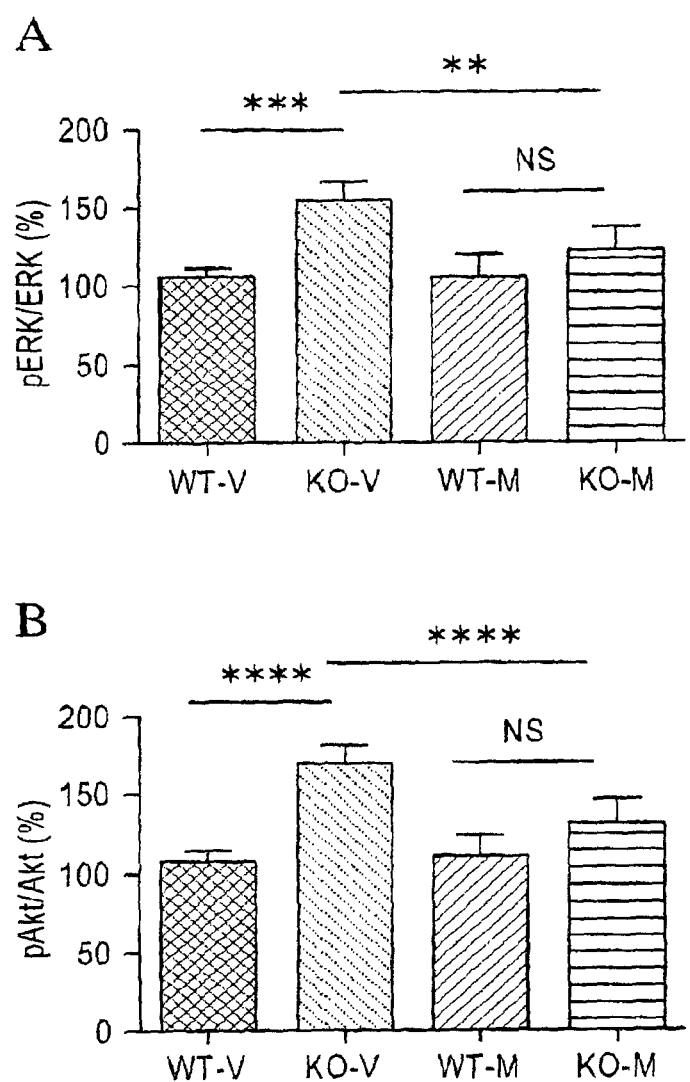
FIG. 6 shows the effect of seven days of once daily intraperitoneal administration of vehicle (V) or 150 mg/kg metadoxine (M) on whole brain levels of phosphorylation of ERK (indicative of ERK activity) (Panel A) and Akt (indicative of Akt activity) (Panel B) in 2-months Fmr1 knockout (KO) or Wild Type (WT) mice. Data shown are mean±scm, N=5 mice per group. $p<0.01$, *$p<0.001$, ****$p<0.0001$, and NS=Not Significant.

Phosphorylation of ERK and Akt:

The effect of seven days of once daily intraperitoneal treatment with either vehicle or 150 mg/kg metadoxine in N=5 Fmr1 knockout or WT mice on whole brain phosphorylation of ERK or Akt in the brain is shown in FIG. 6. Phosphorylation levels were assessed as the ratio of phosphorylated to total ERK. An increase in this ratio indicated activation of ERK. Phosphorylation of ERK was increased in vehicle-treated Fmr1 knockout mice compared to vehicle controls (p<0.001)—this effect replicated the aberrant activation of ERK seen in human subjects with Fragile X Syndrome (Wang et al., 2012). This effect was reduced by metadoxine treatment (p<0.01) such that there was no difference compared to metadoxine-treated WT mice. Metadoxine had no effect on phosphorylation of ERK in WT mice or total ERK levels in any mice. The ratio of phosphorylated Akt to total AKT was also increased in vehicle-treated Fmr1 knockout mice compared to vehicle-treated WT mice (p<0.0001). Treatment with metadoxine reduced the relative levels of phosphorylated Akt in Fmr1 knockout mice (p<0.01), such that Fmr1 knockout mice did not differ from the controls. Metadoxine treatment had no effect on WT mice, or on the total Akt levels of any mice.

Example 3: The Evaluation of Metadoxine in the Fmr1 Knockout Fragile X Mouse Model (Study 2)

Behavioral Effects of Metadoxine in 6 Month Old Fmr1 Knockout Mice

Figure 7:
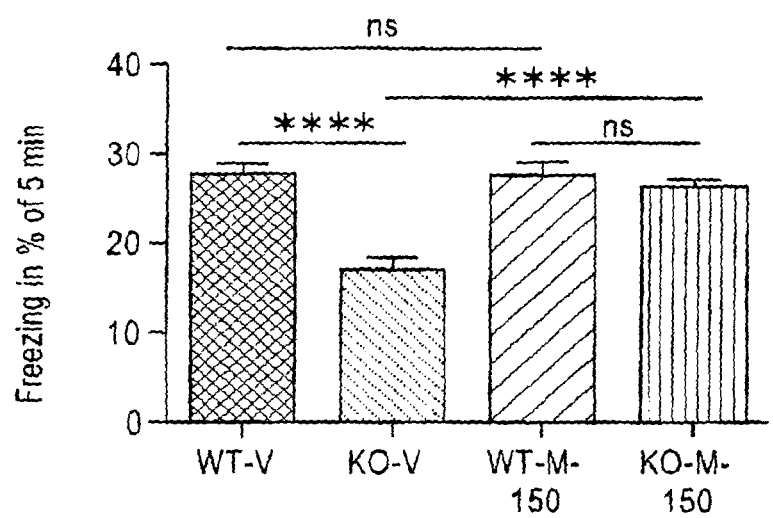
FIG. 7 shows the effect of once daily ip administration of vehicle (V) or 150 mg/kg metadoxine (M) for 7 days in 6 month old Fmr1 knockout (KO) or Wild Type (WT) mice on contextual fear conditioning. Data shown are mean±sem, N=10 mice per group. ****$p<0.0001$ and ns=Not Significant.

Contextual Fear Conditioning:

An initial experiment tested the effect of intraperitoneal administration of vehicle or 150 mg/kg metadoxine once daily for seven days on contextual fear conditioning in groups of N=10 WT and Fmr1 knockout mice aged six months. Vehicle-treated Fmr1 knockout mice (KO-V) showed a deficit in learning in the contextual fear conditioning paradigm when compared with vehicle-treated WT mice (WT-V) as reflected in a reduction in freezing during the test session (FIG. 7 (p<0.0001)). Metadoxine administration reversed the learning deficit effect in Fmr1 knockout mice (p<0.0001 KO-M-150 vs. KO-V). This was a complete reversal such that metadoxine-treated KO mice did not differ from metadoxine-treated WT mice.

Figure 8:
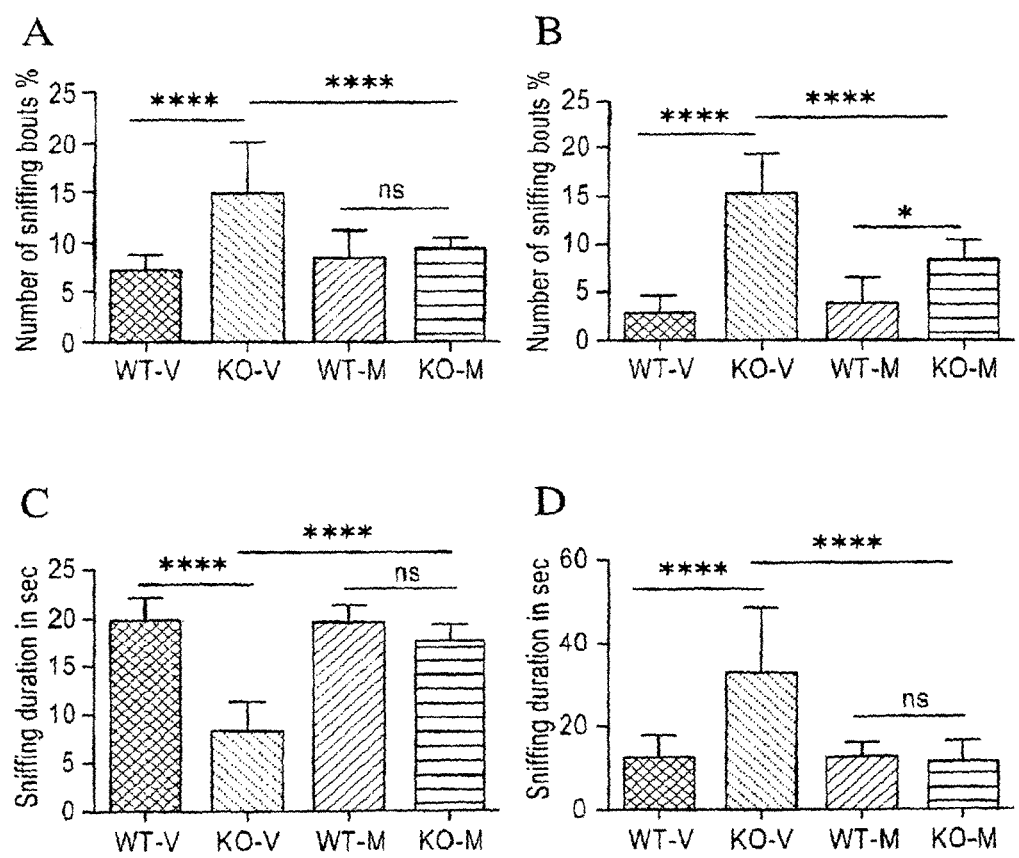
FIG. 8 shows the effect of once daily ip administration of vehicle (V) or 150 mg/kg metadoxine (M) for 7 days in 6 month old Fmr1 knockout (KO) or Wild Type (WT) mice on social approach (Panels A and C) and social memory (Panels B and D) behavior, as measured by number of sniffing bouts or duration of sniffing. Data shown are mean±sem. N=10 mice per group. *$p<0.05$, ****$p<0.0001$, and ns=Not Significant.

Social Approach and Social Memory:

Social approach data (initial Trial 1) are shown in FIG. 8. Panel A (number of sniffing bouts) and Panel C (duration of sniffing). Social memory data (Trial 2, 24 hour after Trial 1) are shown in FIG. 8, Panel B (number of sniffing bouts) and Panel D (duration of sniffing). These results are further discussed below.

During Trial 1, Fmr1 knockout mice showed an increased number of sniffing bouts ($p<0.0001$) (See FIG. 8, Panel A) and a reduced duration of sniffing ($p<0.0001$) (See FIG. 8, Panel C) compared to WT mice. These social interaction deficits are consistent with those reported by other researchers in Fmr1 knockout mice (Thomas et al., 2011). For both number of bouts and duration of sniffing, treatment with metadoxine produced reversals of abnormalities in Fmr1 knockout mice ($p<0.0001$ KO-M-150 vs. KO-V for each), such that metadoxine-treated Fmr1 knockout mice did not differ from metadoxine-treated WT mice for the number of sniffing bouts measurement. Whilst rescue was shown on the duration of sniffing measure, this effect was partial since Fmr1 knockout mice remained different compared to WT mice after metadoxine treatment ($p<0.05$). Metadoxine was without effect on WT mice. These data showed that abnormal social approach behaviors in Fmr1 knockout mice were rescued by metadoxine.

During Trial 2, Fmr1 knockout mice showed both an increase in number of sniffing bouts and an increase in duration of sniffing ($p<0.0001$ for each measure, FIG. 8, Panels B and D, respectively) compared to Wild Type mice. This reflected a failure of habituation and therefore, a social memory deficit. Metadoxine treatment reduced these differences ($p<0.0001$ for KO-M-150 vs. KO-V). The reversal for number of sniffing bouts was partial since a difference remained between metadoxine-treated Fmr1 knockout mice and metadoxine-treated WT mice ($p<0.05$). The reversal by metadoxine was complete for sniffing duration, since no difference was observed between metadoxine-treated Fmr1 knockout and metadoxine-treated WT mice. Metadoxine treatment was without effect on WT mice. These data showed that metadoxine reduced social memory impairments in Fmr1 knockout mice. This reduction in social memory deficit is illustrated below by a calculation of the social memory ratio (described in Example 1):

Social memory ratio was defined as the duration of sniffing bouts: trial 2/trial 1+2. Therefore, an example of no memory was (e.g. $20/(20+20)=0.5$, while an example of memory was (e.g. $10/(20+10)=<0.5$.

The calculated social memory ratios were as follows:

WT-V Trial 2/trial 1+Trial 2: $12.4/12.4+26.8=0.3$, <0.5 memory

KO-V Trial 2/trial 1+Trial 2: $325/325+24.1=0.9$, No memory

WT-M Trial 2/trial 1+Trial 2: $12.5/38.5+12.5=0.2$, <0.5 memory

KO-M Trial 2/trial 1+Trial 2: $12.7/28.4+12.7=0.3$, <0.5 memory

Biochemical Effects of Metadoxine in 6 Month Old Fmr1 Knockout Mice

Figure 9:
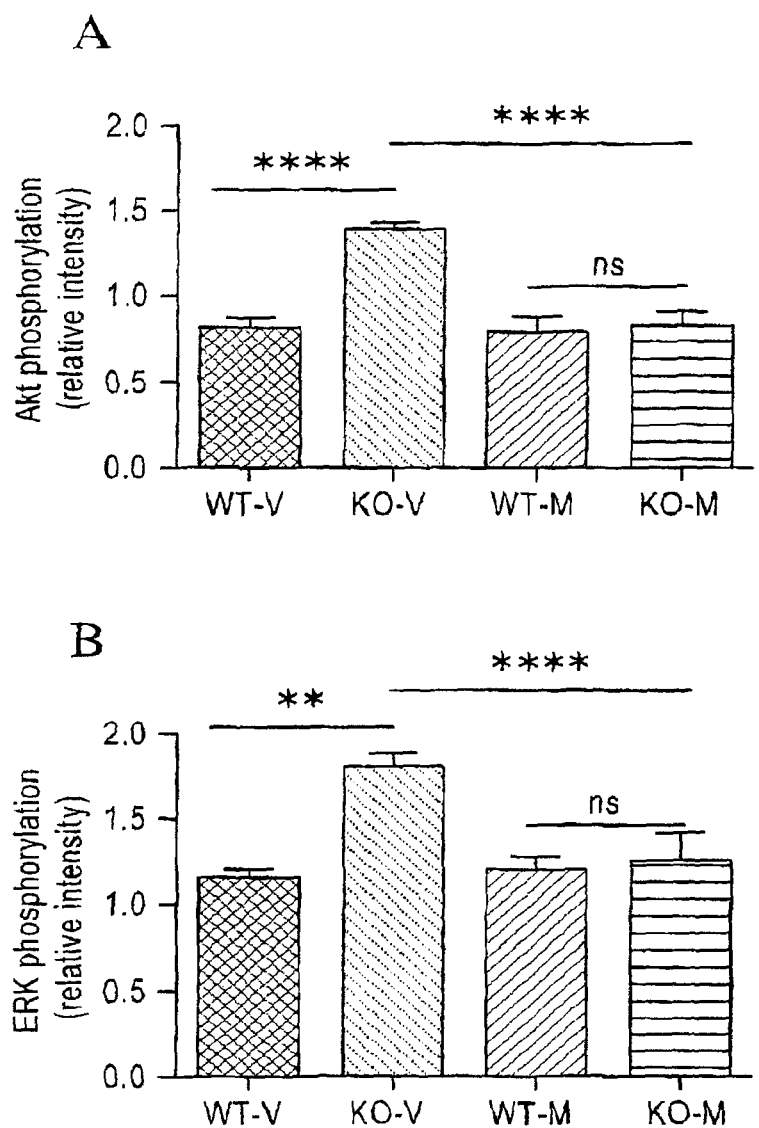
FIG. 9 shows the effect of once daily ip administration of vehicle (V) or 150 mg/kg metadoxine (M) for 7 days on whole brain levels of phosphorylation of ERK (Panel A) and Akt (Panel B) in 6 month old Fmr1 knockout (KO) or Wild Type (WT) mice. Data shown are mean±sem, N=10 mice per group. *$p<0.05$, $p<0.01$, **$p<0.0001$, and ns=Not Significant.

The effect of seven days of once daily ip treatment with either vehicle or 150 mg/kg metadoxine in N=10 Fmr1 knockout or WT mice on whole brain pERK (FIG. 9, Panel A) and pAkt (FIG. 9, Panel B) in the brain following the behavioral tests described above is shown in FIG. 9. Specifically, FIG. 9, Panel A shows brain levels of pAkt, which were increased in Fmr1 knockout mice compared to WT mice as seen in previous experiments ($P<0.0001$). Treatment with metadoxine reversed this increase in brain pAkt ($p<0.0001$ for KO-M-150 vs. KO-V) such that metadoxine-treated Fmr1 knockout mice did not differ from metadoxine-treated WT mice. FIG. 9, Panel B shows brain levels of pERK which were increased in Fmr1 knockout mice compared to WT mice as seen in previous experiments ($p<0.0001$ for KO-M-150 vs. KO-V). This increase was reversed by metadoxine treatment ($p<0.0001$) such that metadoxine-treated Fnmr1 knockout mice did not differ from metadoxine-treated WT mice.

Figure 10:
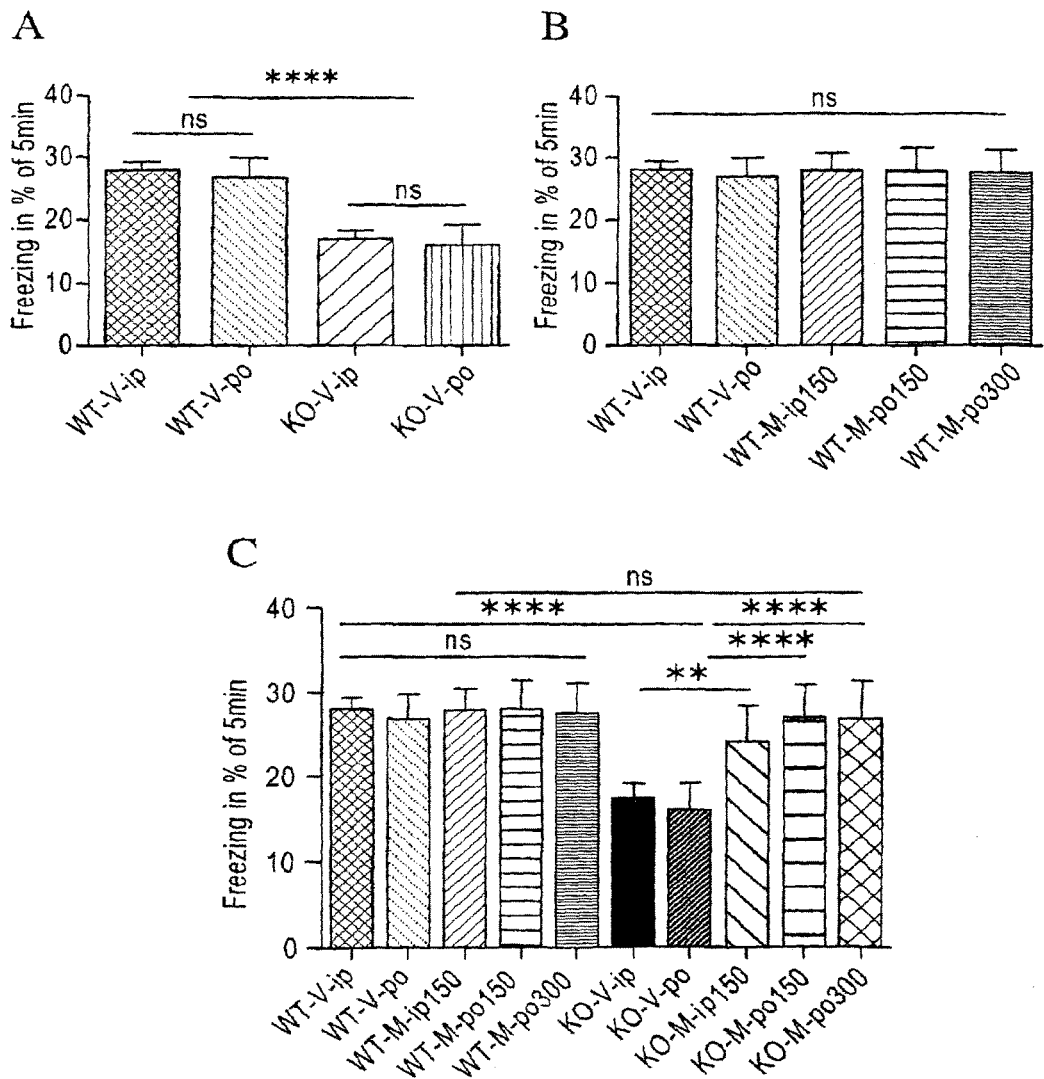
FIG. 10 shows the effect of once daily metadoxine (M) at 150 mg/kg ip or oral administration (po) of vehicle (V) or metadoxine at 150 and 300 mg/kg for 7 days on contextual fear conditioning in 2 month old Fmr1 knockout (KO) or Wild Type (WT) mice. Data shown are mean±sem, N=10 mice per group. Specifically, Panel A shows ip and oral treatment with vehicle in Fmr1 knockout and Wild Type mice. Panel B shows ip and oral treatment with metadoxine in Wild Type mice. Panel C shows ip and oral treatment with metadoxine in Fmr1 knockout mice. $p<0.01$, **$p<0.0001$, and ns=Not Significant.

Effect of Metadoxine Following Intraperitoneal or Oral Administration on the Behavior of 2 Month Old Mice FIG. 10 shows the effect of administration of once daily metadoxine at doses of 150 mg/kg ip or 150 and 300 mg/kg orally for seven days on contextual fear conditioning in two month old Fmr1 knockout and WT mice. Specifically, FIG. 10, Panel A shows contextual fear conditioning data from Fmr1 knockout and WT mice after ip and oral treatment with vehicle. There were no differences related to the route of administration of vehicle. Fmr1 knockout mice showed a reduction in freezing behavior compared to WT mice after vehicle treatment via ip and oral routes ($p<0.0001$ in each case). FIG. 10, Panel B shows the effect of metadoxine treatment via both routes of administration in WT mice. No effects were seen. FIG. 10, Panel C shows that ip 150 mg/kg and oral 150 and 300 mg/kg metadoxine treatment in Fnmr1 knockout mice reversed the decrease in freezing behavior seen in Fmr1 knockout mice ($p<0.01$, $p<0.0001$, and $p<0.0001$, for KO-M-ip, KO-M-po150, and KO-M-po 300 vs. KO-V-ip and KO-V po, respectively). The effect of administration with 150 mg po metadoxine did not differ from the effect of administration of 300 mg/kg po metadoxine. The effect of 150 and 300 mg/kg oral metadoxine in Fmr1 knockout mice did not differ from the effect of 150 mg/kg ip metadoxine. In each case, the reversal was complete since metadoxine-treated Fmr1 knockout mice did not differ from metadoxine-treated WT mice.

Figure 11:
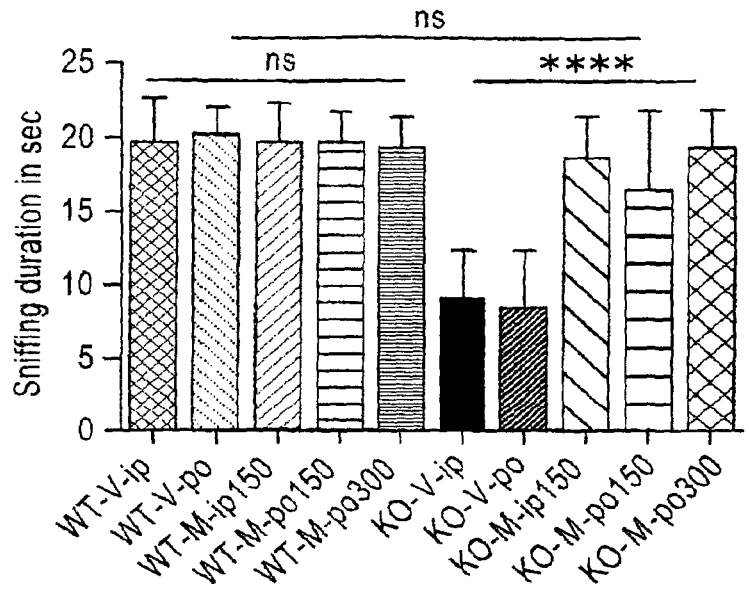
FIG. 11 shows the effect of once daily ip or oral administration (po) of vehicle (V) or metadoxine (M) at 150 or 300 mg/kg for 7 days on social approach (Panel A) and social memory (Panel B) in 2 month old Fmr1 knockout (KO) or Wild Type (WT) mice. Data shown are mean±sem, N=10 mice per group. $p<0.01$, **$p<0.0001$, and ns=Not Significant.
Figure 11:
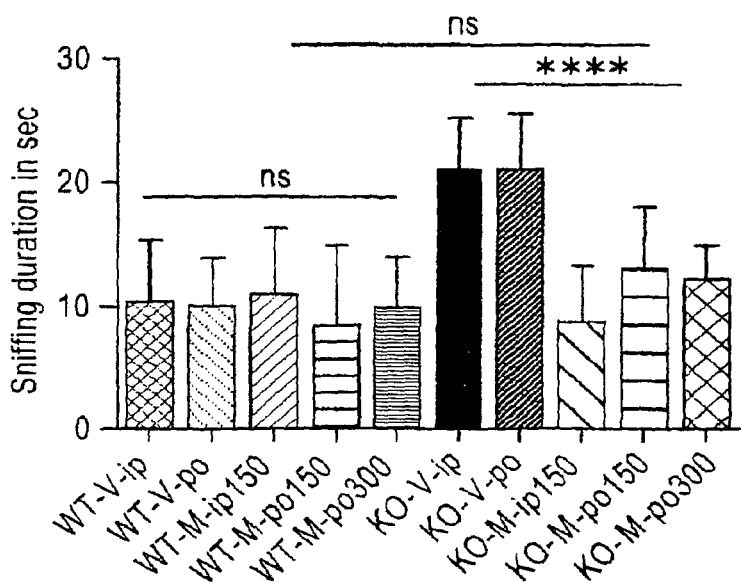

FIG. 11 shows the effect of administration of once daily metadoxine at doses of 150 mg/kg ip or 150 and 300 mg/kg orally for seven days on social approach and social memory in Fmr1 knockout and WT mice. Specifically, FIG. 11, Panel A shows the effect of vehicle or metadoxine at 150 mg/kg ip or 150 and 300 mg/kg orally on social approach behavior in Fmr1 knockout or WT mice. After ip or oral treatment with vehicle, the duration of sniffing behavior in Fmr1 knockout mice was reduced compared to WT mice ($p<0.0001$ for each). Metadoxine treatment at any dose was without effect on WT mice. However, metadoxine treatment at 150 mg/kg ip, 150 mg/kg, and 300 mg/kg orally produced reversals of the social approach deficit seen in Fmr1 knockout mice ($p<0.0001$ for KO-M-po150 and KO-M-po300 vs. KO-V po, respectively). The effect of oral metadoxine was not dose dependent between 150 and 300 mg/kg. This reversal was complete since metadoxine-treated Fmr1 knockout mice did not differ from metadoxine-treated WT mice. The effect of 150 mg/kg ip metadoxine in Fmr1 knockout mice did not differ from the effect of 150 mg/kg oral or 300 mg/kg oral metadoxine. FIG. 11, Panel B shows the effect of vehicle or metadoxine at 150 mg/kg ip or 150 and 300 mg/kg orally on social memory in Fmr1 knockout or WT mice. After ip or oral treatment with vehicle, the duration of sniffing behavior in Fmr1 knockout mice was increased compared to WT mice ($p<0.0001$ for each). Metadoxine treatment at any dose was without effect on WT mice. However, metadoxine treatment at 150 mg/kg ip, 150 mg/kg orally, and 300 mg/kg orally produced reversals of the social approach deficit seen in Fmr1 knockout mice ($p<0.0001$, $p<0.05$, and $p<0.01$ for KO-M-ip 150, KO-M-po150, and KO-M-po 300 vs. KO-V- ip and KO-V po, respectively). This reversal was complete since metadoxine-treated Fmr1 knockout mice did not differ from metadoxine-treated WT mice. The effect of 150 mg/kg ip metadoxine in Fmr1 knockout mice did not differ from the effect of 150 mg/kg oral or 300 mg/kg oral metadoxine. Also, there was no dose dependency for the effects of oral metadoxine treatment between 150 mg/kg and 300 mg/kg.

Figure 12:
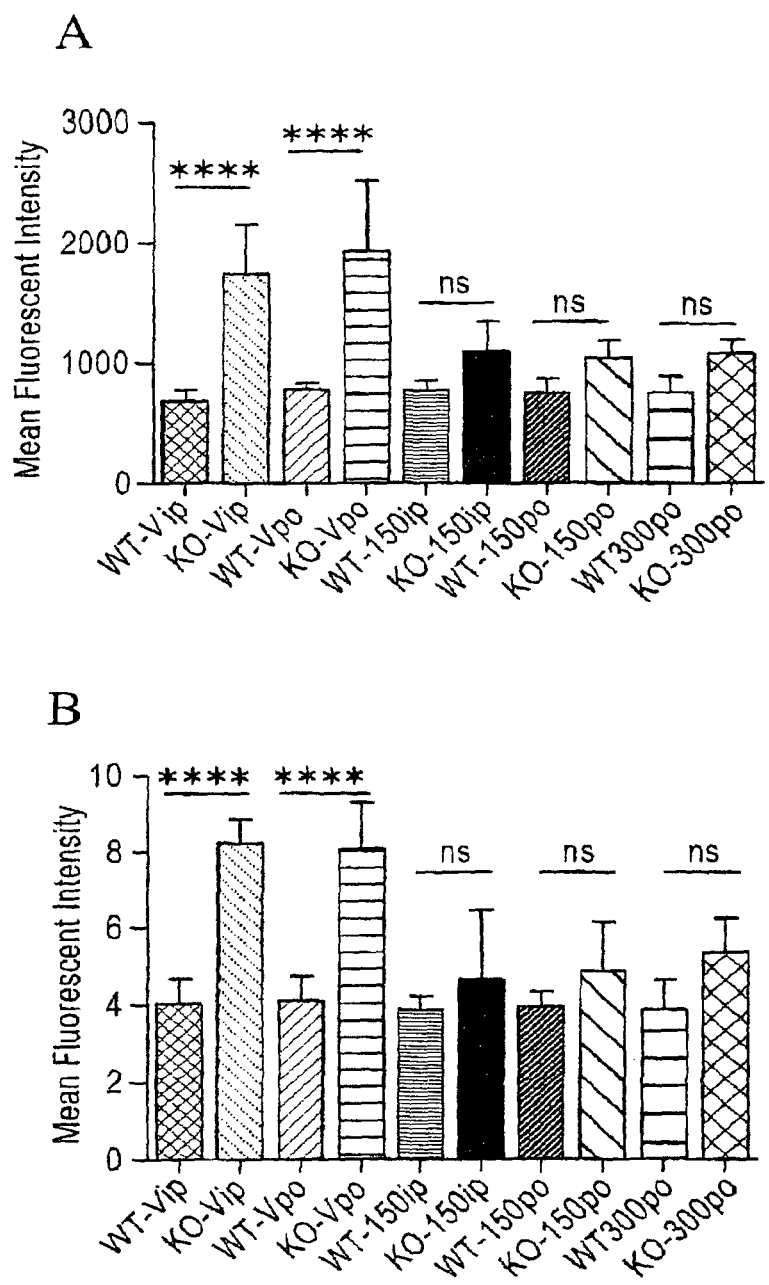
FIG. 12 shows the effect of once daily ip or oral administration (po) of vehicle (V) or metadoxine (M) at 150 or 300 mg/kg for 7 days on lymphocyte biomarkers as assessed using flow cytometry in 2 month old Fnmr1 knockout (KO) and Wild Type (WT) mice. Biomarkers shown are pAkt (Panel A) and pERK (Panel B) in Fmr1 knockout or Wild Type mice. Data shown are mean±sem, N=10 mice per group. ****$p<0.0001$ and ns=Not Significant.

Effect of Metadoxine on Biochemical Markers Following Intraperitoneal or Oral Administration in 2 Month Old Mice Peripheral Lymphocytes:

FIG. 12 shows the effect of administration of once daily metadoxine at doses of 150 mg/kg ip or 150 mg/kg and 300 mg/kg orally for 7 days on lymphocyte pAkt (FIG. 12, Panel A) and pERK (FIG. 12, Panel B) as determined by flow cytometry in two month old Fmr1 knockout and WT mice. Specifically, FIG. 12, Panel A shows that vehicle-treated Fmr1 knockout mice exhibited increased phosphorylation of lymphocyte Akt ($p<0.0001$ for both ip and oral administration) compared to WT mice receiving equivalent vehicle treatment. Treatment with once daily metadoxine at 150 mg/kg ip or oral doses of 150 mg/kg or 300 mg/kg for 7 days normalized overactivated Akt, such that pAkt levels did not differ between metadoxine-treated Fmr1 knockout mice and WT mice receiving the same treatment. FIG. 12, Panel B shows that vehicle-treated Fmr1 knockout mice showed increased phosphorylation of lymphocyte ERK ($p<0.0001$ for both ip and oral administration) compared to WT mice receiving equivalent vehicle treatment. Treatment with once daily metadoxine at 150 mg/kg ip or oral doses of 150 mg/kg or 300 mg/kg for 7 days normalized overactivated ERK such that pERK levels did not differ between metadoxine-treated Fnmr1 knockout mice and WT mice receiving the same treatment.

Figure 13:
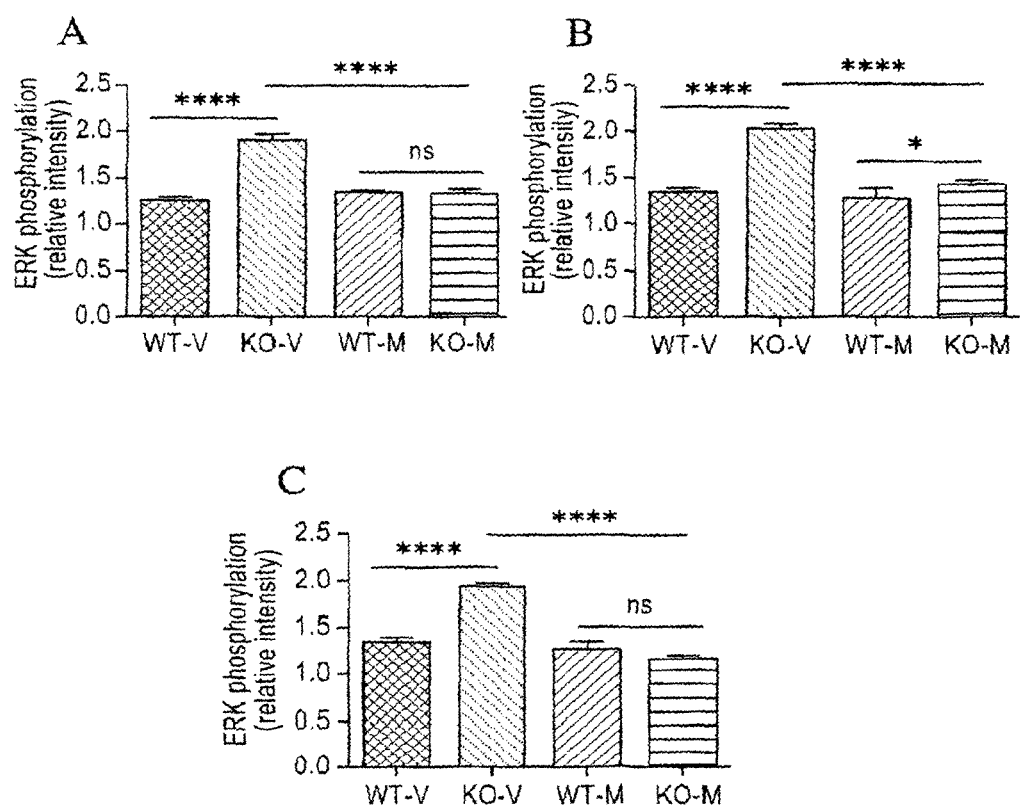
FIG. 13 shows the effect of once daily ip of vehicle (V) or 150 mg/kg metadoxine (M) for 7 days on pERK levels in brain regions of two month old Wild Type (WT) and Fmr1 knockout (KO) mice. The regions analyzed were the hippocampus (Panel A), pre-frontal cortex (Panel B), and striatum (Panel C) in Fmr1 knockout or Wild Type mice. Data shown are mean±sem, N=10 mice per group. ****p<0.0001 and ns=Not Significant.

Brain Regions:

FIG. 13 shows the effect of administration of 150 mg/kg metadoxine for seven days on pERK levels in hippocampus, pre-frontal cortex, and striatum. pERK levels were increased in Fmr1 knockout mice compared to WT mice in all three brain regions ($p<0.0001$ in all cases). pERK levels were decreased in metadoxine-treated Fmr1 knockout mice compared to vehicle-treated Fmr1 knockout mice ($p<0.0001$ in all cases). There were no differences between KO-M and WT-M groups in the hippocampus and striatum, showing complete reversal of activation of ERK. The effect in pre-frontal cortex was partial, the KO-V and KO-M groups remained different ($p<0.05$). Metadoxine was without effect on WT mice.

FIG. 14 shows the effect of administration of 150 mg/kg metadoxine for seven days on pAkt levels in hippocampus, pre-frontal cortex and striatum. pAkt levels were increased in Fmr1 knockout mice compared to WT mice in all three brain regions ($p<0.0001$ in all cases). pAkt levels were decreased in metadoxine-treated Fmr1 knockout mice compared to vehicle-treated Fmr1 knockout mice in all three brain regions ($p<0.0001$ in all cases). In all cases, there were no differences between KO-M and WT-M groups, showing complete reversal of activation of Akt. Metadoxine was without effect on WT mice. Reduction in brain and blood elevated levels of phosphorylated ERK and Akt correlated with the improved behavioral outcomes of Fmr1 knockout mice, suggesting that the phosphorylation levels are biomarkers of metadoxine treatment response Effects of Metadoxine on Dendritic Filopodia Density and Maturation in Primary Hippocampal Neurons from Fmr1 Knockout Mice In Vitro FIG. 15 (Panels A-C) shows the effect of treatment for five hours with 300 μM metadoxine. Dendrites were divided into 10 segments of 10 μm, each based on distance from the soma (proximal to distal, left to right). Spine density was increased in neurons from Fmr1 knockout mice compared to neurons from WT mice in segment 3. Specifically, FIG. 15, Panel A shows the density of neuronal filopodia. Primary hippocampal neurons from Fmr1 knockout mice displayed an increased density of filopodia ($p<0.001$). Treatment with 300 M metadoxine reduced the aberrant increase in density of neuronal filopodia in Fmr1 knockout mice ($p<0.001$). Neurons from Fmr1 knockout mice showed filopodia with characteristics of immaturity, being longer (FIG. 15, Panel B ($p<0.01$)) and narrower (FIG. 15, Panel C ($p<0.01$)). Treatment with metadoxine reversed this increase in filopodia length (FIG. 15, Panel B ($p<0.01$)) and reversed the decrease in width (FIG. 15, Panel C ($p<0.001$)).

Effects of Metadoxine on De Novo Hippocampal Protein Synthesis in the Fmr1 Knockout Mouse In Vitro FIG. 16 shows the effect of treatment with either vehicle or 300 μM metadoxine on basal de novo protein synthesis in 400 M hippocampal slices from Fmr1 knockout or WT mice. Protein synthesis was higher in vehicle-treated hippocampi from Fmr1 knockout mice than vehicle-treated WT control hippocampi ($p<0.0001$). Metadoxine treatment reduced protein synthesis rates in Fmr1 knockout mouse hippocampi. This effect was partial since hippocampi from Fmr1 knockout mice retained higher protein synthesis rates than metadoxine-treated hippocampi from WT mice ($p<0.001$).

TABLE 1

Summary of Effects of Metadoxine (150 mg/kg) in the Mouse Model of Fragile X Syndrome

| Test | Route/ | Abnormal in fmr1 KO mice (Y/N) | Reduction of deficit (Y/N) | Replication of Previous Study |
|---|---|---|---|---|
| Behavioral effects in 6 month old mice | | | | |
| Contextual fear conditioning | 150 mg/kg | Deficit | Y | Y |
| Social approach | 150 mg/kg | Y | Y | Y |
| Social memory | 150 mg/kg | Y | Y | Not tested |
| Biochemical effects in 6 month old mice | | | | |
| Phosphorylation of brain Akt | 150 mg/kg | Increased in fmr1 KO mice | Y | Y |
| Phosphorylation of brain ERK | 150 mg/kg | Increased in fmr1 KO mice | Y | Y |
| Phosphorylation of brain GSK3β (tyr219/tyr279) | 150 mg/kg i.p. | Increased in fmr1 KO mice | N | Not tested |
| Brain GST levels | 150 mg/kg | Decreased in fmr1 KO mice | Y | Y |

TABLE 1-continued

Summary of Effects of Metadoxine (150 mg/kg) in the Mouse Model of Fragile X Syndrome

| Test | Route/ | Abnormal in fmr1 KO mice (Y/N) | Reduction of deficit (Y/N) | Replication of Previous Study |
|---|---|---|---|---|
| Behavioral effects of Metadoxine following intraperitoneal or oral administration in 2 month old mice | | | | |
| Contextual fear conditioning | 150 mg/kg ip | Y | Y | Y |
| Social approach behaviour | 150 mg/kg ip | Y | Y | Y |
| Social memory | 150 mg/kg ip | Y | Y | Not tested |
| Contextual fear conditioning | 150 mg/kg po | Y | Y | Not tested |
| Social approach behaviour | 150 mg/kg po | Y | Y | Not tested |
| Social memory | 150 mg/kg po | Y | Y | Not tested |
| Contextual fear conditioning | 300 mg/kg po | Y | Y | Not tested |
| Social approach behaviour | 300 mg/kg po | Y | Y | Not tested |
| Social memory | 300 mg/kg po | Y | Y | Not tested |
| Biochemical effects of Metadoxine following intraperitoneal or oral administration in 2 month old mice | | | | |
| Lymphocyte pAkt and pERK | 150 mg/kg ip | Increased | Y | Not tested |
| Lymphocyte pGSK3β (tyr219/tyr279) | 150 mg/kg ip | Increased | N | Not tested |
| Lymphocyte GST | 150 mg/kg ip | Decreased | N | Not tested |
| Lymphocyte pAkt and pERK | 150 mg/kg po | Increased | Y | Not tested |
| Lymphocyte pGSK3β(tyr219/tyr279) | 150 mg/kg po | Increased | N | Not tested |
| Lymphocyte GST | 150 mg/kg po | Decreased | N | Not tested |
| Lymphocyte pAkt and pERK | 300 mg/kg po | Increased | Y | Not tested |
| Lymphocyte pGSK3β(tyr219/tyr279) | 300 mg/kg po | Increased | N | Not tested |
| Lymphocyte GST | 300 mg/kg po | Decreased | N | Not tested |
| Hippocampal pERK | 150 mg/kg ip | Increased | Y | Not tested |
| Prefrontal cortex pERK | 150 mg/kg ip | Increased | Y | Not tested |
| Striatum pERK | 150 mg/kg ip | Increased | Y | Not tested |
| Hippocampal pAkt | 150 mg/kg ip | Increased | Y | Not tested |
| Prefrontal cortex pAkt | 150 mg/kg ip | Increased | Y | Not tested |
| Striatum pAkt | 150 mg/kg ip | Increased | Y | Not tested |
| Hippocampal pGSK3β(ser9) | 150 mg/kg ip | Normal levels | NA | Not tested |
| Prefrontal cortex pGSK3βS(ser9) | 150 mg/kg ip | Decreased | N | Not tested |
| Striatum pGSK3β(ser9) | 150 mg/kg ip | Decreased | Y | Not tested |
| Hippocampal GST | 150 mg/kg ip | Decreased | N | Not tested |
| Prefrontal cortex GST | 150 mg/kg ip | Decreased | N | Not tested |
| Striatum GST | 150 mg/kg ip | Decreased | Y | Not tested |
| Hippocampal pS6K1(ser235/236) | 150 mg/kg ip | Increased | N | Not tested |
| Prefrontal cortex pS6K1(ser235/236) | 150 mg/kg ip | Increased | N | Not tested |
| Striatum pS6K1(ser235/236) | 150 mg/kg ip | Increased | N | Not tested |
| Hippocampal pS6K1(ser240/244) | 150 mg/kg ip | Increased | N | Not tested |
| Prefrontal cortex pS6K1(ser240/244) | 150 mg/kg ip | Increased | N | Not tested |
| Striatum pS6K1(ser240/244) | 150 mg/kg ip | Increased | N | Not tested |
| Effects of Metadoxine on filopodia density and maturation in neurons from fmr1 knockout mice in vitro | | | | |
| Neuronal filopodia density | 300 μM | Increased | Y | Not tested |
| Neuronal filopodia length | 300 μM | Increased | Y | Not tested |
| Neuronal filopodia width | 300 μM | Decreased | Y | Not tested |
| Effects of Metadoxine on de novo hippocampal protein synthesis in fmr1 knockout mice in vitro | | | | |
| De novo hippocampal protein synthesis | 300 μM | Increased | Y | Not tested |

We claim:

1. A method of treating or alleviating a symptom of Fragile X Syndrome in a subject who has Fragile X Syndrome, comprising administering to the subject a composition comprising metadoxine.

2. The method of claim 1, comprising administering a total per day dose-of-metadoxine of between 100-3000 mg.

3. The method of claim 1, wherein the metadoxine is administered daily, every other day or weekly.

4. The method of claim 1, wherein the metadoxine is administered in one, two, or three dosage forms per day.

5. The method of claim 1, wherein the metadoxine is administered in a sustained release oral dosage form, wherein the metadoxine is formulated as a combination of slow release and immediate release forms.

6. The method of claim 5, wherein:
  (a) the slow release form provides for sustained release of the metadoxine for at least 8 hours; and
  (b) wherein relative proportion of the slow release metadoxine to the immediate release metadoxine is between about 60:40 and 80:20.

7. The method of claim 6, wherein the relative proportion of the slow release metadoxine to the immediate release metadoxine is about 65:35.

8. The method of claim 1, wherein the symptom is impaired learning or impaired sociability.

* * * * *